United States Patent
Yamamoto et al.

(10) Patent No.: US 7,816,475 B2
(45) Date of Patent: Oct. 19, 2010

(54) AMINOALKOXYSTYRENE, PROCESS FOR PREPARATION THEREOF, POLYMER THEREOF, PROCESS FOR PRODUCING THE POLYMER AND USE THEREOF

(75) Inventors: Takashi Yamamoto, Shunan (JP); Shin-ichi Ishikawa, Shunan (JP); Yasuhiro Oda, Shunan (JP); Hisao Eguchi, Shunan (JP)

(73) Assignee: Tosoh Corporation, Yamaguchi (JP)

( * ) Notice: Subject to any disclaimer, the term of this patent is extended or adjusted under 35 U.S.C. 154(b) by 900 days.

(21) Appl. No.: 11/713,087

(22) Filed: Mar. 2, 2007

(65) Prior Publication Data
US 2007/0213490 A1 Sep. 13, 2007

(30) Foreign Application Priority Data
Mar. 2, 2006 (JP) .............................. 2006-056602
Mar. 2, 2006 (JP) .............................. 2006-056603

(51) Int. Cl.
*C08F 12/08* (2006.01)
*C08F 12/28* (2006.01)
(52) U.S. Cl. .................. 526/310; 526/312; 526/346; 526/347
(58) Field of Classification Search .................. 526/310, 526/312, 346, 347
See application file for complete search history.

(56) References Cited

U.S. PATENT DOCUMENTS
4,857,493 A * 8/1989 Ford et al. .................. 502/159

FOREIGN PATENT DOCUMENTS
JP 63-91660 * 4/1988

OTHER PUBLICATIONS
Inokuma, Seiichi et al., "Photochemical Synthesis of Diazacryptophane", Chemistry Letters, 1998, vol. 4, pp. 287-288.

* cited by examiner

*Primary Examiner*—Helen L. Pezzuto
(74) *Attorney, Agent, or Firm*—Foley & Lardner LLP

(57) ABSTRACT

An aminoalkoxystyrene represented by the formula (1)

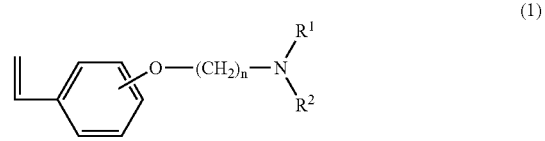

wherein $R^1$ and $R^2$ are $C_{1-4}$ alkyl and n is 3-6. The aminoalkoxystyrene is prepared by reacting an aminoalkoxyphenylmagnesium halide with vinyl halide in the presence of a catalyst. A quaternized amino group-containing polymer made by quaternizing the amino groups of a polymer prepared from the aminoalkoxystyrene is useful as an anion exchanger.

3 Claims, No Drawings

AMINOALKOXYSTYRENE, PROCESS FOR PREPARATION THEREOF, POLYMER THEREOF, PROCESS FOR PRODUCING THE POLYMER AND USE THEREOF

BACKGROUND OF THE INVENTION

(1) Field of the Invention

This invention relates to a novel aminoalkoxystyrene which is expected to be a raw material for a functional polymer, a process for preparing the aminoalkoxystyrene, a polymer of the aminoalkoxystyrene, a process for producing the polymer, and use of the polymer.

(2) Description of the Related Art

The aminoalkoxystyrene according to the present invention is a novel compound and a process for preparing the compound is also not known.

Styrene derivatives analogous to the aminoalkoxystyrene of the present invention are known. For example, a process for preparing amino group-containing styrene derivatives has been proposed in Chemistry Letters, Japan, 1998, vol. 4, p 287-288 (Scheme 1), wherein a tosylated p-(2-hydroxyethoxy) bromobenzene, which is prepared by reacting p-bromophenol with 2-chloroethanol, followed by tosylation, is allowed to react with tributylvinyltin in the presence of a palladium catalyst to synthesize p-(2-tosyloxyethoxy)styrene, and then, the tosyloxy group of this compound is substituted by an amino compound. This process has problems for the preparation of the aminoalkoxystyrene according to the present invention because the toxic tin compound must be used in a large amount and the palladium catalyst is expensive.

Styrene derivatives having an amino group or an ammonium group in side chain or chains are widely known as an anion exchanger. The aminoalkoxystyrene according to the present invention is also expected to be useful as an anion exchanger.

As specific examples of anion exchangers, there can be mentioned strong basic anion exchangers comprising a combination of an ion exchange group including an anion exchange group such as a nitrogen- or phosphorus-containing group, for example, quaternary ammonium group and phosphonium group, with a polymeric material such as polystyrene, polyacrylate, polymethacrylate, polyvinyl alcohol or polyvinyl-allylamine. Of these, polymeric anion exchangers comprising repeating units of trimethylaminomethylstyrene are widely used.

The polymeric anion exchangers comprising repeating units of trimethylaminomethylstyrene are produced, for example, by a process wherein a styrene-divinylbenzene copolymer is reacted with chloromethyl methyl ether, and the thus-chloromethylated copolymer is reacted with trimethylamine (see, for example, Synthetic Resin Industry Technique 10, Ion Exchange Resin-Phenolic Resin, Japan, 1963, p 9-12 (Anion Exchange Resin). This process has problems such that chloromethyl methyl ether is carcinogenic, and the trimethylaminomethylstyrene structure is not stable, namely, trimethylamine and methyl group readily leave therefrom at a temperature higher than room temperature, and thus, the duration of life is short when the anion exchangers are used at a high temperature, or the anion exchangers must be used at a low temperature. Trimethylamine is readily eluted and exhales an offensive amine odor, and the amount of materials eluted from the anion exchangers is undesirably large.

SUMMARY OF THE INVENTION

Objects of the present invention are to provide novel aminoalkoxystyrenes which are expected to be a raw material for a functional polymer; and a process for preparing the aminoalkoxystrenes with an enhanced efficiency.

Other objects of the present invention are to provide a polymer prepared from the aminoalkoxystyrene, a process for producing the polymer, and use of the polymer.

Thus, in one aspect of the present invention, there is provided an aminoalkoxystyrene represented by the following general formula (1)

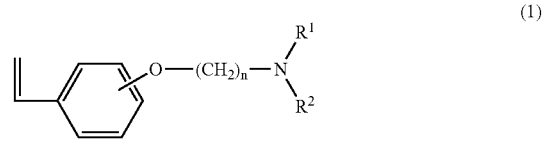

wherein $R^1$ and $R^2$ independently represent an alkyl group having 1 to 4 carbon atoms, and n is an integer of 3 to 6.

In another aspect of the present invention, there is provided a process for preparing the above-mentioned aminoalkoxystyrene, which comprises allowing an aminoalkoxyphenyl-magnesium halide represented by the following general formula (2) to react with a vinyl halide represented by the following general formula (3) in the presence of a catalyst;

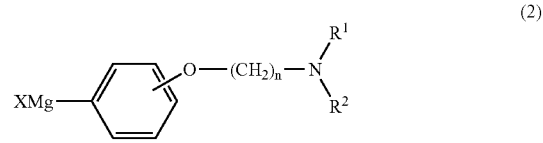

wherein $R^1$, $R^2$ and n are the same as defined above with respect to formula (1), and X represents a halogen atom,

wherein X represents a halogen atom.

In still another aspect of the present invention, there is provided a polymer comprising structural units represented by the following general formula (4):

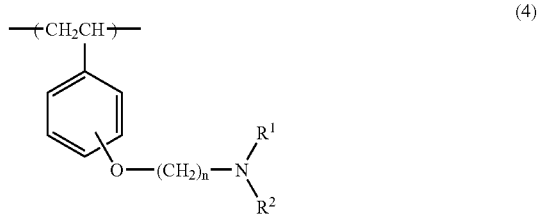

wherein $R^1$, $R^2$ and n are the same as defined above with respect to formula (1).

In a further aspect of the present invention, there is provide a process for producing the polymer comprising structural units of formula (4), which comprises homopolymerizing the aminoalkoxystyrene of formula (1), or copolymerizing the aminoalkoxystyrene of formula (1) with other vinyl monomer.

In a further aspect of the present invention, there is provide a polymer comprising structural units represented by the following general formula (5):

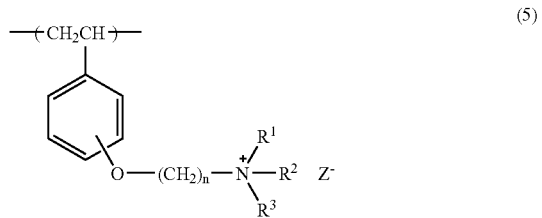

(5)

wherein $R^1$ and $R^2$ independently represent an alkyl group having 1 to 4 carbon atoms, $R^3$ represents an alkyl group having 1 to 4 carbon atoms or an alkanol group having 1 to 4 carbon atoms, Z represents an anion, and n is an integer of 3 to 6.

In a further aspect of the present invention, there is provide a process for producing the polymer comprising structural units of formula (5), which comprises allowing the polymer comprising structural units of formula (4), to react with an alkyl halide represented by the following general formula (6):

(6)

wherein $R^3$ represents an alkyl group having 1 to 4 carbon atoms or an alkanol group having 1 to 4 carbon atoms, and Y represents a halogen atom.

In a further aspect of the present invention, there is provide an anion exchanger comprising the polymer comprising structural units of formula (5).

DESCRIPTION OF THE PREFERRED EMBODIMENTS

The aminoalkoxystyrene according to the present invention is represented by the following general formula (1)

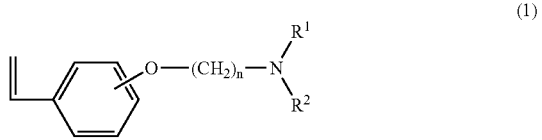

(1)

wherein $R^1$ and $R^2$ independently represent an alkyl group having 1 to 4 carbon atoms, and n is an integer of 3 to 6.

The alkyl group having 1 to 4 carbon atoms includes, for example, a methyl group, an ethyl group, a n-propyl group, an i-propyl group, a n-butyl group, an i-butyl group, a s-butyl group and a t-butyl group.

As specific examples of the aminoalkoxystyrene, there can be mentioned p-(3-N,N-dimethylaminopropoxy)styrene, p-(3-N,N-diethylaminopropoxy)styrene, p-(3-N,N-di-n-propyl-aminopropoxy)styrene, p-(3-N,N-di-i-propylaminopropoxy)styrene, p-(3-N,N-di-n-butylaminopropoxy)styrene, p-(3-N,N-di-i-butylaminopropoxy)styrene, p-(3-N,N-di-s-butyl-aminopropoxy) styrene, p-(3-N,N-di-t-butylaminopropoxy) styrene, p-(4-N,N-dimethylaminobutoxy)styrene, p-(4-N,N-diethyl-aminobutoxy) styrene, p-(4-N,N-di-n-propylaminobutoxy) styrene, p-(4-N,N-di-i-propylaminobutoxy)styrene, p-(4-N,N-di-n-butyl-aminobutoxy)styrene, p-(4-N,N-di-i-butylaminobutoxy)styrene, p-(4-N,N-di-s-butylaminobutoxy)styrene, p-(4-N,N-di-t-butyl-aminobutoxy) styrene, p-(5-N,N-dimethylaminopentyloxy) styrene, p-(5-N,N-diethylaminopentyloxy) styrene, p-(5-N,N-di-n-propyl-aminopentyloxy)styrene, p-(5-N,N-di-i-propylaminopentyloxy)styrene, p-(5-N,N-di-n-butylaminopentyloxy)styrene, p-(5-N,N-di-i-butylaminopentyloxy)styrene, p-(5-N,N-di-s-butylaminopentyloxy)styrene, p-(5-N,N-di-t-butylaminopentyloxy)styrene, p-(6-N,N-dimethyl-aminohexyloxy) styrene, p-(6-N,N-diethylaminohexyloxy)styrene, p-(6-N,N-di-n-propylaminohexyloxy)styrene, p-(6-N,N-di-i-propylaminohexyloxy)styrene, p-(6-N,N-di-n-butylaminohexyloxy)styrene, p-(6-N,N-di-i-butylaminohexyloxy)styrene, p-(6-N,N-di-s-butylaminohexyloxy)styrene, p-(6-N,N-di-t-butylaminohexyloxy)styrene, m-(3-N,N-dimethyl-aminopropoxy)styrene, m-(3-N,N-diethylaminopropoxy) styrene, m-(3-N,N-di-n-propylaminopropoxy)styrene, m-(3-N,N-di-i-propylaminopropoxy)styrene, m-(3-N,N-di-n-butylaminopropoxy) styrene, m-(3-N,N-di-i-butylaminopropoxy)styrene, m-(3-N,N-di-s-butylaminopropoxy) styrene, m-(3-N,N-di-t-butylaminopropoxy)styrene, m-(4-N,N-dimethylaminobutoxy)styrene, m-(4-N,N-diethylaminobutoxy) styrene, m-(4-N,N-di-n-propylaminobutoxy) styrene, m-(4-N,N-di-i-propylaminobutoxy) styrene, m-(4-N,N-di-n-butyl-aminobutoxy)styrene, m-(4-N,N-di-i-butylaminobutoxy)styrene, m-(4-N,N-di-s-butylaminobutoxy) styrene, m-(4-N,N-di-t-butyl-aminobutoxy) styrene, m-(5-N,N-dimethylaminopentyloxy) styrene, m-(5-N,N-diethylaminopentyloxy) styrene, m-(5-N,N-di-n-propyl-aminopentyloxy)styrene, m-(5-N,N-di-i-propylarainopentyloxy)styrene, m-(5-N,N-di-n-butylaminopentyloxy)styrene, m-(5-N,N-di-i-butylaminopentyloxy)styrene, m-(5-N,N-di-s-butylaminopentyloxy)styrene, m-(5-N,N-di-t-butylaminopentyloxy)styrene, m-(6-N,N-dimethyl-aminohexyloxy) styrene, m-(6-N,N-diethylaminohexyloxy) styrene, m-(6-N,N-di-n-propylaminohexyloxy)styrene, m-(6-N,N-di-i-propylaminohexyloxy)styrene, m-(6-N,N-di-n-butylaminohexyloxy)styrene, m-(6-N,N-di-i-butylaminohexyloxy)styrene, m-(6-N,N-di-s-butylaminohexyloxy)styrene, m-(6-N,N-di-t-butylaminohexyloxy)styrene, o-(3-N,N-dimethyl-aminopropoxy)styrene, o-(3-N,N-diethylaminopropoxy)styrene, o-(3-N,N-di-n-propylaminopropoxy)styrene, o-(3-N,N-di-i-propylaminopropoxy)styrene, o-(3-N,N-di-n-butylaminopropoxy) styrene, o-(3-N,N-di-i-butyl-aminopropoxy) styrene, o-(3-N,N-di-s-butylaminopropoxy) styrene, o-(3-N,N-di-t-butylaminopropoxy)styrene, o-(4-N,N-dimethyl-aminobutoxy)styrene, o-(4-N,N-diethylaminobutoxy)styrene, o-(4-N,N-di-n-propylaminobutoxy)styrene, o-(4-N,N-di-i-propylaminobutoxy)styrene, o-(4-N,N-di-n-butyl-aminobutoxy)styrene, o-(4-N,N-di-i-butylaminobutoxy)styrene, o-(4-N,N-di-s-butylaminobutoxy)styrene, o-(4-N,N-di-t-butyl-aminobutoxy)styrene, o-(5-N,N-dimethylaminopentyloxy) styrene, o-(5-N,N-diethylaminopentyloxy)styrene, o-(5-N,N-di-n-propyl-aminopentyloxy)styrene, o-(5-N,N-di-i-propylaminopentyloxy)-styrene, o-(5-N,N-di-n-butylaminopentyloxy)styrene, o-(5-N,N-di-i- butylaminopentyloxy)styrene, o-(5-N,N-di-e-butylaminopentyloxy)styrene, o-(5-N,N-di-t-butylaminopentyloxy)styrene, o-(6-N,N-dimethylaminohexyloxy) styrene, o-(6-N,N-diethylaminohexyloxy) styrene, o-(6-N,N-di-n-propylaminohexyloxy)styrene, o-(6-N,N-di-i-propylaminohexyloxy)styrene, o-(6-N,N-di-n-butylaminohexyloxy)styrene, o-(6-N,N-di-i-butylaminohexyloxy)styrene, o-(6-N,N-di-s-butylaminohexyloxy)styrene, o-(6-N,N-di-t-butylaminohexyloxy)styrene, p-(3-N-methyl-N-ethylaminopropoxy)styrene, p-(3-N-methyl-N-n-propylamino-propoxy)styrene, p-(3-N-methyl-N-i-propylaminopropoxy)styrene, p-(3-N-methyl-N-n-butylaminopropoxy) styrene, p-(3-N-methyl-N-i-butylaminopropoxy)styrene, p-(3-N-methyl-N-s-butylaminopropoxy)styrene, p-(3-N-methyl-N-t-butylamino-propoxy) styrene, p-(3-N-ethyl-N-n-propylaminopropoxy) styrene, p-(3-N-ethyl-N-i-propylaminopropoxy)styrene, p-(3-N-ethyl-N-n-butylaminopropoxy)styrene, p-(3-N-ethyl-N-i-butylaminopropoxy)styrene, p-(3-N-ethyl-N-s-butylaminopropoxy) styrene, p-(3-N-ethyl-N-t-butylaminopropoxy)styrene, p-(3-N-n-propyl-N-1-propylaminopropoxy)styrene, p-(3-N-n-propyl-N-n-butyl-aminopropoxy) styrene, p-(3-N-n-propyl-N-i-butylaminopropoxy)styrene, p-(3-N-n-propyl-N-s-butylaminopropoxy)styrene, p-(3-N-n-propyl-N-t-butylaminopropoxy)styrene, p-(3-N-i-propyl-N-n-butylaminopropoxy)styrene, m-(3-N-methyl-N-ethylaminopropoxy)styrene, m-(3-N-methyl-N-n-propylaminopropoxy)styrene, m-(3-N-methyl-N-i-propylaminopropoxy)styrene, m-(3-N-methyl-N-n-butylaminopropoxy)styrene, m-(3-N-methyl-N-i-butylaminopropoxy)styrene, m-(3-N-methyl-N-s-butylaminopropoxy)styrene, m-(3-N-methyl-N-t-butylaminopropoxy)styrene, m-(3-N-ethyl-N-n-propylamino-propoxy) styrene, m-(3-N-ethyl-N-i-propylaminopropoxy) styrene, m-(3-N-ethyl-N-n-butylaminopropoxy) styrene, m-(3-N-ethyl-N-i-butylaminopropoxy)styrene, m-(3-N-ethyl-N-s-butylaminopropoxy)styrene, m-(3-N-ethyl-N-t-butylaminopropoxy) styrene, m-(3-N-n-propyl-N-i-propylaminopropoxy)styrene, m-(3-N-n-propyl-N-n-butylaminopropoxy)styrene, m-(3-N-n-propyl-N-i-butylaminopropoxy)styrene, m-(3-N-n-propyl-N-s-butylaminopropoxy)styrene, m-(3-N-n-propyl-N-t-butylaminopropoxy)styrene, m-(3-N-i-propyl-N-n-butylaminopropoxy)styrene, o-(3-N-methyl-N-ethylaminopropoxy)styrene, o-(3-N-methyl-N-n-propylaminopropoxy)styrene, o-(3-N-methyl-N-i-propylaminopropoxy)styrene, o-(3-N-methyl-N-n-butylaminopropoxy)styrene, o-(3-N-methyl-N-i-butylaminopropoxy)styrene, o-(3-N-methyl-N-s-butylaminopropoxy)styrene, o-(3-N-methyl-N-t-butylaminopropoxy)styrene, o-(3-N-ethyl-N-n-propylamino-propoxy) styrene, o-(3-N-ethyl-N-i-propylaminopropoxy) styrene, o-(3-N-ethyl-N-n-butylaminopropoxy)styrene, o-(3-N-ethyl-N-i-butylaminopropoxy)styrene, o-(3-N-ethyl-N-s-butylaminopropoxy)styrene, o-(3-N-ethyl-N-t-butylaminopropoxy) styrene, o-(3-N-n-propyl-N-i-propylaminopropoxy)styrene, o-(3-N-n-propyl-N-n-butylaminopropoxy)styrene, o-(3-N-n-propyl-N-i-butylaminopropoxy)styrene, o-(3-N-n-propyl-N-s-butylaminopropoxy) styrene, o-(3-N-n-propyl-N-t-butylaminopropoxy)styrene and o-(3-N-i-propyl-N-n-butylaminopropoxy)styrene.

The aminoalkoxystyrene of the present invention can be produced with an enhanced efficiency by a process according to the present invention, which comprises allowing an aminoalkoxyphenylmagnesium halide represented by the following general formula (2) to react with a vinyl halide represented by the following general formula (3) in the presence of a catalyst;

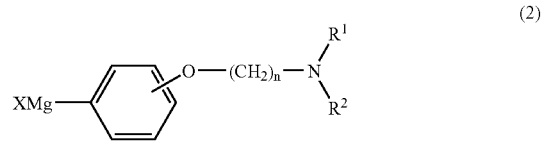

wherein $R^1$ and $R^2$ independently represent an alkyl group having 1 to 4 carbon atoms, X represents a halogen atom, and n is an integer of 3 to 6,

wherein X represents a halogen atom.

The aminoalkoxyphenylmagnesium halide represented by formula (2) is not particularly limited, and, as specific examples thereof, there can be mentioned
(3-N,N-dimethylaminopropoxy)phenylmagnesium halide,
(3-N,N-diethylaminopropoxy)phenylmagnesium halide,
(3-N,N-di-n-propylaminopropoxy)phenylmagnesium halide,
(3-N,N-di-i-propylaminopropoxy)phenylmagnesium halide,
(3-N,N-di-n-butylaminopropoxy)phenylmagnesium halide,
(3-N,N-di-i-butylaminopropoxy)phenylmagnesium halide,
(3-N,N-di-s-butylaminopropoxy)phenylmagnesium halide,
(3-N,N-di-t-butylaminopropoxy)phenylmagnesium halide,
(4-N,N-dimethylaminobutoxy)phenylmagnesium halide,
(4-N,N-diethylaminobutoxy)phenylmagnesium halide,
(4-N,N-di-n-propylaminobutoxy)phenylmagnesium halide,
(4-N,N-di-i-propylaminobutoxy)phenylmagnesium halide,
(4-N,N-di-n-butylaminobutoxy)phenylmagnesium halide,
(4-N,N-di-i-butylaminobutoxy)phenylmagnesium halide,
(4-N,N-di-s-butylaminobutoxy)phenylmagnesium halide,
(4-N,N-di-t-butylaminobutoxy)phenylmagnesium halide,
(5-N,N-dimethylaminopentyloxy)phenylmagnesium halide,
(5-N,N-diethylaminopentyloxy)phenylmagnesium halide,
(5-N,N-di-n-propylaminopentyloxy)phenylmagnesium halide,
(5-N,N-di-i-propylaminopentyloxy)phenylmagnesium halide,
(5-N,N-di-n-butylaminopentyloxy)phenylmagnesium halide,
(5-N,N-di-i-butylaminopentyloxy)phenylmagnesium halide,
(5-N,N-di-s-butylaminopentyloxy)phenylmagnesium halide,
(5-N,N-di-t-butylaminopentyloxy)phenylmagnesium halide,
(6-N,N-dimethylaminohexyloxy)phenylmagnesium halide,
(6-N,N-diethylaminohexyloxy)phenylmagnesium halide,
(6-N,N-di-n-propylaminohexyloxy)phenylmagnesium halide,
(6-N,N-di-i-propylaminohexyloxy)phenylmagnesium halide,
(6-N,N-di-n-butylaminohexyloxy)phenylmagnesium halide,
(6-N,N-di-i-butylaminohexylaoxy)phenylmagnesium halide,
(6-N,N-di-s-butylaminohexyloxy)phenylmagnesium halide,
(6-N,N-di-t-butylaminohexyloxy)phenylmagnesium halide, (3-N-methyl-N-ethylaminopropoxy)phenylmagnesium halide,
(3-N-methyl-N-n-propylaminopropoxy)phenylmagnesium halide,
(3-N-methyl-N-i-propylaminopropoxy)phenylmagnesium halide,
(3-N-methyl-N-n-butylaminopropoxy)phenylmagnesium halide,
(3-N-methyl-N-i-butylaminopropoxy)phenylmagnesium halide,
(3-N-methyl-N-s-butylaminopropoxy)phenylmagnesium halide,
(3-N-methyl-N-t-butylaminopropoxy)phenylmagnesium halide,
(3-N-ethyl-N-n-propylaminopropoxy)phenylmagnesium halide,
(3-N-ethyl-N-i-propylaminopropoxy)phenylmagnesium halide,
(3-N-ethyl-N-n-butylaminopropoxy)phenylmagnesium halide,
(3-N-ethyl-N-i-butylaminopropoxy)phenylmagnesium halide,
(3-N-ethyl-N-s-butylaminopropoxy)phenylmagnesium halide,
(3-N-ethyl-N-t-butylaminopropoxy)phenylmagnesium halide,
(3-N-n-propyl-N-i-propylaminopropoxy)phenylmagnesium halide,
(3-N-n-propyl-N-n-butylaminopropoxy)phenylmagnesium halide,
(3-N-n-propyl-N-i-butylaminopropoxy)phenylmagnesium halide,
(3-N-n-propyl-N-s-butylaminopropoxy)phenylmagnesium halide,
(3-N-n-propyl-N-t-butylaminopropoxy)phenylmagnesium halide
and (3-N-i-propyl-N-n-butylaminopropoxy)phenylmagnesium halide.

The halide includes chloride, bromide, iodide and fluoride.

The process for preparing the above-mentioned aminoalkoxyphenylmagnesium halide is not particularly limited. The aminoalkoxyphenylmagnesium halide can be easily prepared according to the following reaction scheme (A):

Reaction Scheme (A)

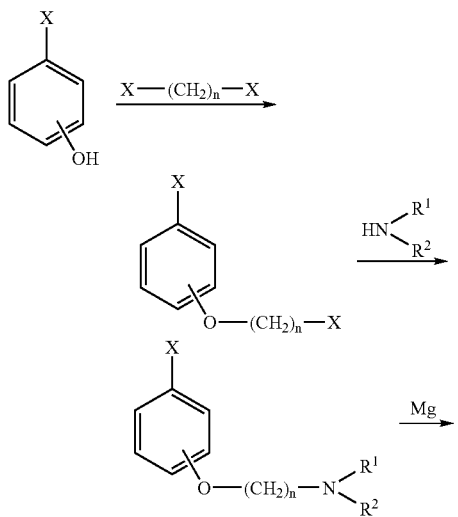

-continued

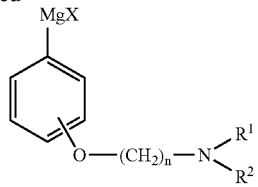

wherein $R^1$ and $R^2$ independently represent an alkyl group having 1 to 4 carbon atoms, X represents a halogen atom and n is an integer of 3 to 6. According to this reaction scheme, a halophenol is reacted with a dihaloalkane to give a haloalkoxyphenyl halide; the haloalkoxyphenyl halide is reacted with a secondary amine compound to give an aminoalkoxy-halobenzene; and then the aminoalkoxy-halobenzene is reacted with metallic magnesium.

As specific examples of the halophenol used in the process according to reaction scheme (A), there can be mentioned o-fluorophenol, o-chlorophenol, o-bromophenol, o-iodophenol, m-fluorophenol, m-chlorophenol, m-bromophenol, m-iodophenol, p-fluorophenol, p-chlorophenol, p-bromophenol and p-iodophenol.

As specific examples of the dihaloalkane used in the process according to reaction scheme (A), there can be mentioned 1-chloro-3-fluoropropane, 1,3-dichloropropane, 1-bromo-3-chloropropane, 1-chloro-3-iodopropane, 1-bromo-3-fluoropropane, 1,3-dibromopropane, 1-brom-3-iodopropane, 1-fluoro-3-iodopropane, 1,3-diiodopropane, 1-chloro-4-fluorobutane, 1,4-dichlorobutane, 1-bromo-4-chlorobutane, 1-chloro-4-iodobutane, 1-bromo-4-fluorobutane, 1,4-dibromobutane, 1-bromo-4-iodobutane, 1-fluoro-4-iodobutane, 1,4-diiodobutane, 1-chloro-5-fluoropentane, 1,5-dichloropentane, 1-bromo-5-chloropentane, 1-chloro-5-iodopentane, 1-bromo-5-fluoropentane, 1,5-dibromopentane, 1-brom-5-iodopentane, 1-fluoro-5-iodopentane, 1,5-diiodopentane, 1-chloro-6-fluorohexane, 1,6-dichlorohexane, 1-bromo-6-chlorohexane, 1-chloro-6-iodohexane, 1-bromo-6-fluorohexane, 1,6-dibromohexane, 1-bromo-6-iodohexane, 1-fluoro-6-iodohexane and 1,6-diiodohexane.

In the production process of the present invention, the aminoalkoxyphenylmagnesium halide is reacted with vinyl halide in the presence of a catalyst to give the target aminoalkoxystyrene.

The catalyst used in the process for the preparation of the aminoalkoxystyrene is not particularly limited, and includes, for example, palladium catalysts, nickel catalysts, manganese catalysts, iron catalysts, cobalt catalysts and rhodium catalysts. These catalysts may be used either alone or as a combination of at least two thereof.

The palladium catalysts refer to catalysts containing palladium element as a catalytically active ingredient, and are not particularly limited, and, as specific examples thereof, there can be mentioned palladium powder, palladium (II) chloride, palladium (II) bromide, palladium (II) iodide, palladium (II) acetate, palladium (II) nitrate, palladium (II) sulfate, palladium (II) cyamide, palladium (II) acetylacetonate, palladium (II) trifluoroacetate, palladium carbon, hydrates of these compounds, and complexes of these compounds.

The nickel catalysts refer to catalysts containing nickel element as a catalytically active ingredient, and are not particularly limited, and, as specific examples thereof, there can be mentioned nickel powder, nickel (II) fluoride, nickel (II) chloride, nickel (II) bromide, nickel (II) iodide, nickel (II) sulfate, nickel (II) nitrate, nickel (II) perchlorate, nickel (II)

sulfide, nickel (II) formate, nickel (II) oxalate, nickel (II) acetate, nickel (II) fumarate, nickel (II) lactate, nickel (II) gluconate, nickel (II) benzoate, nickel (II) stearate, nickel (II) sulfamate, nickel (II) amidosulfate, nickel (II) carbonate, nickel (II) acetylacetonate, nickel carbon, hydrates of these compounds, and complexes of these compounds.

The manganese catalysts refer to catalysts containing manganese element as a catalytically active ingredient, and are not particularly limited, and, as specific examples thereof, there can be mentioned manganese (II) chloride, manganese (II) bromide, manganese (II) iodide, manganese (II) fluoride, manganese (II) acetate, manganese (III) acetate, manganese (II) formate, manganese (II) oxalate, manganese (II) benzoate, manganese (II) stearate, manganese (II) borate, manganese (II) acetylacetonate, manganese (III) acetylacetonate, manganese (II) carbonate, manganese (II) sulfate, manganese (II) nitrate, manganese (II) phosphate, manganese powder, hydrates of these compounds, and complexes of these compounds.

The iron catalysts refer to catalysts containing iron element as a catalytically active ingredient, and are not particularly limited, and, as specific examples thereof, there can be mentioned iron (II) chloride, iron (III) chloride, iron (II) bromide, iron (III) bromide, iron (II) iodide, iron (II) fluoride, iron (III) fluoride, iron (II) acetate, iron (II) oxalate, iron (III) oxalate, iron (III) citrate, iron (III) perchlorate, iron (III) acetylacetonate, iron (III) nitrate, iron (III) phosphate, iron (II) sulfate, iron (III) sulfate, iron powder, hydrates of these compounds, and complexes of these compounds.

The cobalt catalysts refer to catalysts containing cobalt element as a catalytically active ingredient, and are not particularly limited, and, as specific examples thereof, there can be mentioned cobalt (II) chloride, cobalt (II) bromide, cobalt (II) iodide, cobalt (II) fluoride, cobalt (II) acetate, cobalt (III) acetate, cobalt (II) formate, cobalt (II) oxalate, cobalt (II) benzoate, cobalt (II) stearate, cobalt (II) borate, cobalt (II) acetylacetonate, cobalt (III) acetylacetonate, cobalt (II) carbonate, cobalt (II) sulfate, cobalt (II) nitrate, cobalt (II) phosphate, cobalt powder, hydrates of these compounds, and complexes of these compounds.

The rhodium catalysts refer to catalysts containing rhodium element as a catalytically active ingredient, and are not particularly limited, and, as specific examples thereof, there can be mentioned rhodium (II) chloride, rhodium (II) bromide, rhodium (II) acetate, rhodium (III) acetate, rhodium (II) acetylacetonate, rhodium (III) acetylacetonate, rhodium powder, rhodium carbon, hydrates of these compounds, and complexes of these compounds.

The above-recited catalysts may be used either alone or as a mixture comprising at least two thereof.

The amount of catalyst used in the preparation process of the present invention is not particularly limited, but is usually in the range of $1\times10^{-4}$ to 0.1 mol per mol of the aminoalkoxyphenylmagnesium halide. When the amount of catalyst is smaller than $1\times10^{-4}$ mol, the reaction does not proceed at a desired rate. In contrast, when the amount of catalyst is larger than 0.1 mol, the yield of the target compound increases only to a minor extent with an increase of the catalyst amount, and thus the preparation process is economically disadvantageous.

In the process for preparing the aminoalkoxystyrene according to the present invention, an aminoalkoxyphenylmagnesium halide of formula (2) is allowed to react with a vinyl halide of formula (3) in the presence of the above-mentioned catalyst usually an inert gas atmosphere such as nitrogen and/or argon.

As specific examples of the vinyl halide, there can be mentioned vinyl fluoride, vinyl chloride, vinyl bromide and vinyl iodide. These vinyl halides may be used either alone or as a combination of at least two thereof. In view of availability and cost consideration, vinyl chloride and vinyl bromide are preferable. The amount of vinyl halide is not particularly limited, but is usually in the range of 1.0 to 10.0 mols per mol of the aminoalkoxyphenylmagnesium halide. When the amount of vinyl halide is smaller than 1.0 mol, the rate of reaction is low. In contrast, when the amount of vinyl halide is larger than 10.0 mol, the yield of the target compound increases only to a minor extent with an increase of the amount of vinyl halide, and thus the preparation process is economically disadvantageous.

The above-mentioned reaction in the preparation process of the present invention is usually carried out in the presence of a reaction medium. No limitation is imposed to the reaction medium provided that it does not give harmful influence to the reaction. The reaction medium includes, for example, ether solvents, oxygen-containing solvents, nitrogen-containing solvents, aromatic hydrocarbon solvents and aliphatic hydrocarbon solvents. These reaction mediums may be used either alone or as a combination of at least two thereof.

The above-mentioned reaction is carried out usually at a temperature of $-10°$ C. to the reflux temperature of reaction medium.

After completion of the reaction, inorganic substances produced by side reactions and unreacted raw materials are removed from a reaction mixture by adopting an appropriate combination of at least two selected from acid washing, water washing and alkali washing. Further, purification by chromatography, distillation and/or recrystallization is carried out to give the target aminoalkoxystyrene.

The polymer according to the present invention comprises structural units represented by the following general formula (4):

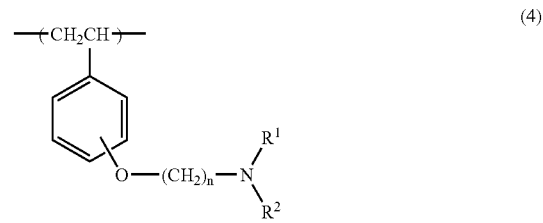

wherein $R^1$ and $R^2$ independently represent an alkyl group having 1 to 4 carbon atoms, and n is an integer of 3 to 6.

The polymer includes is a homopolymer consisting of the structural units of formula (4), and a copolymer comprising at least 1% by mol of structural units of formula (4) and not more than 99% by mol of structural units derived from other copolymerizable monomer. The copolymer preferably comprises 1% to 99% by mol of structural units of formula (4) and 99% to 1% by mol of structural units derived from other copolymerizable vinyl monomer.

The process for polymerizing the aminoalkoxystyrene is not particularly limited, and, conventional radical polymerization processes including solution polymerization, bulk polymerization, suspension polymerization and emulsion polymerization processes can be employed. An anion polymerization process can also be employed.

The radical polymerization process can be carried out, for example, by maintaining the aminoalkoxystyrene and an optional copolymerizable vinyl monomer or monomers at a temperature of 30 to $200°$ C. in the presence of a radical polymerization initiator while being stirred in an appropriate organic solvent in a nitrogen or other inert gas atmosphere.

As specific examples of the radical polymerization initiator, there can be mentioned azo compounds such as 2,2'-azobisisobutyronitrile, 2,2'-azobis-(2,4-dimethyl-valeronitrile), 2,2'-azobis-(4-methoxy-2,4-dimethyl-valeronitrile), 2,2'-azobismethylbutyronitrile, 2,2'-azobiscyclohexanecarbonitrile, cyanomethylethyl-azoformamide, 2,2'-azobis(2,4-dimethylpropionate) and 2,2'-azobiscyanovaleric acid; and organic peroxides such as benzoyl peroxide, lauroyl peroxide, 1,1'-bis-(t-butylperoxy)-cyclohexane, 3,5,5-trimethyl-hexanoyl peroxide and t-butyl peroxy-2-ethylhexanoate; and hydrogen peroxide. Radical-containing polymeric substrates can also be used as a radical polymerization initiator, which are prepared by irradiating a polymeric substrate such as polyethylene film, polyethylene nonwoven fabric, polypropylene film or polypropylene nonwoven fabric with radiation such as electronic rays or γ-rays. A polymerization aid such as 2,2,6,6-tetramethyl-1-piperidinyloxy, iodine, mercaptan or a styrene dimer can be additionally used.

The anion polymerization process can be carried out, for example, by maintaining the aminoalkoxystyrene and an optional copolymerizable vinyl monomer or monomers at a temperature of −100 to 50° C. in the presence of an anion polymerization initiator while being stirred in an appropriate organic solvent in a nitrogen or other inert gas atmosphere.

The anion polymerization initiator includes, for example, organoalkali metals such as n-butyllithium, s-butyllithium, t-butyllithium, ethyllithium, ethylsodium, 1,1-diphenyl-hexyl-lithium and 1,1-diphenyl-3-methylpentyllithium.

Alternatively, the polymerization for producing the above-mentioned polymer can also be carried out by heating without use of a polymerization initiator, or, by a cation polymerization process.

As specific examples of the organic solvent appropriately used in the above-mentioned polymerization process, there can be mentioned ketones such as acetone, methyl ethyl ketone and methyl amyl ketone; ethers such as diethyl ether and tetrahydrofuran (THF); water; alcohols such as methanol, ethanol and propanol; aliphatic hydrocarbons such as hexane, heptane and octane; aromatic hydrocarbons such as benzene, toluene and xylene; alkyl halides such as chloroform, bromoform, methylene chloride, methylene bromide and carbon tetrachloride; esters such as ethyl acetate, butyl acetate, ethyl lactate, propylene glycol monomethyl ether, propylene glycol monomethyl ether acetate and cellosolve; and non-protonic polar solvents such as dimethylformamide, dimethylsulfoxide and hexamethylphosphoramide.

As specific examples of other vinyl monomers copolymerizable with the aminoalkoxystyrene, there can be mentioned styrenic monomers such as styrene, methylstyrene, dimethyletyrene, trimethylstyrene, ethylstyrene, propylstyrene, cyclohexylstyrene, chloromethylstyrene, trifluoromethylstyrene, ethoxymethystyrene, acetoxymethylstyrene, methoxystyrene, dimethoxystyrene, t-butoxystyrene, acetoxystyrene, 1-ethoxyethoxystyrene, chlorostyrene, dichlorostyrene, bromostyrene, iodostyrene, fluorostyrene, carboxystyrene, styrenesulfonic acid, methyl styrenesulfonate, ethyl styrenesulfonate and cyclohexyl styrenesulfonate; methacrylic acid ester monomers such as methyl methacrylate, ethyl methacrylate, n-propyl methacrylate, i-propyl methacrylate, n-butyl methacrylate, i-butyl methacrylate, sec-butyl methacrylate, t-butyl methacrylate, amyl methacrylate, 2-ethylhexyl methacrylate, dodecyl methacrylate, chloroethyl methacrylate, 2-hydroxyethyl methacrylate, 2-hydroxypropyl methacrylate, 5-hydroxypentyl methacrylate, cyclohexyl methacrylate, allyl methacrylate, trimethylolpropane monomethacrylate, pentaerythritol monomethacrylate, glycidyl methacrylate, benzyl methacrylate, methoxybenzyl methacrylate, chlorobenzyl methacrylate, hydroxybenzyl methacrylate, hydroxyphenethyl methacrylate, dihydroxyphenethyl methacrylate, furfuryl methacrylate, tetrahydrofurfuryl methacrylate, phenyl methacrylate, hydroxyphenyl methacrylate, chlorophenyl methacrylate, sulfamoylphenyl methacrylate and 2-(hydroxyphenylcarbonyloxy)ethyl methacrylate; acrylic acid ester monomers such as methyl acrylate, ethyl acrylate, n-propyl acrylate, i-propyl acrylate, n-butyl acrylate, i-butyl acrylate, sec-butyl acrylate, t-butyl acrylate, amyl acrylate, 2-ethylhexyl acrylate, dodecyl acrylate, chloroethyl acrylate, 2-hydroxyethyl acrylate, 2-hydroxypropyl acrylate, 5-hydroxypentyl acrylate, cyclohexyl acrylate, allyl acrylate, trimethylolpropane monoacrylate, pentaerythritol monoacrylate, benzyl acrylate, methoxybenzyl acrylate, chlorobenzyl acrylate, hydroxybenzyl acrylate, hydroxyphenethyl acrylate, dihydroxyphenethyl acrylate, furfuryl acrylate, tetrahydrofurfuryl acrylate, phenyl acrylate, hydroxyphenyl acrylate, chlorophenyl acrylate, sulfamoylphenyl acrylate and 2-(hydroxyphenylcarbonyloxy) ethyl acrylate; and crosslinkable monomers such as divinylbenzene, trivinylbenzene, divinyltoluene, divinylnaphthalene, ethylene glycol dimethacrylate and ethylene glycol diacrylate.

The polymer used as an anion exchanger according to the present invention comprises structural units represented by the following general formula (5);

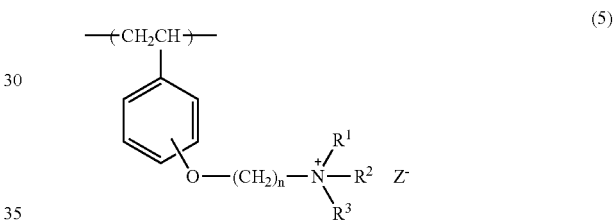

(5)

wherein $R^1$ and $R^2$ independently represent an alkyl group having 1 to 4 carbon atoms, $R^3$ represents an alkyl group having 1 to 4 carbon atoms or an alkanol group having 1 to 4 carbon atoms, Z represents an anion, and n is an integer of 3 to 6.

The alkyl group having 1 to 4 carbon atoms includes, for example, a methyl group, an ethyl group, a n-propyl group, an i-propyl group, a n-butyl group, an i-butyl group, a s-butyl group and a t-butyl group. The alkanol group having 1 to 4 carbon atoms includes, for example, a hydroxymethyl group, a hydroxyethyl group, 3-hydroxypropyl group and 4-hydroxybutyl group.

The anion is not particularly limited, and includes, for example, a halogen anion, a hydroxyl anion and a carbonate anion.

The polymer comprising structural units of formula (5) used as an anion exchanger can be produced by a process wherein a polymer comprising structural units represented by the following general formula (4):

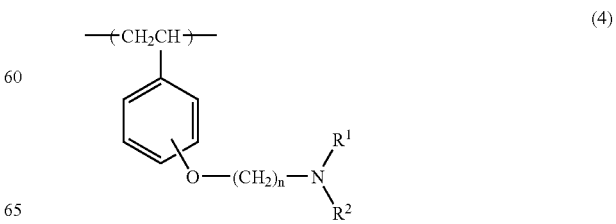

(4)

wherein $R^1$ and $R^2$ independently represent an alkyl group having 1 to 4 carbon atoms, and n is an integer of 3 to 6, is allowed to react with an alkyl halide represented by the following general formula (6):

$$R^3\text{—}Y \qquad (6)$$

wherein $R^3$ represents an alkyl group having 1 to 4 carbon atoms or an alkanol group having 1 to 4 carbon atoms, and Y represents a halogen atom.

The polymer comprising structural units of formula (4) includes a homopolymer consisting of the structural units of formula (4), and a copolymer comprising at least 1% by mol of structural units of formula (4) and not more than 99% by mol of structural units derived from other copolymerizable monomer. The copolymer preferably comprises 1% to 99% by mol of structural units of formula (4) and 99% to 1% by mol of structural units derived from other copolymerizable vinyl monomer.

As specific examples of the alkyl halide of formula (6), there can be mentioned methyl chloride, methyl bromide, methyl iodide, ethyl chloride, ethyl bromide, ethyl iodide, n-propyl chloride, n-propyl bromide, n-propyl iodide, i-propyl chloride, i-propyl bromide, i-propyl iodide, n-butyl chloride, n-butyl bromide, n-butyl iodide, i-butyl chloride, i-butyl bromide, i-butyl iodide, s-butyl chloride, s-butyl bromide, s-butyl iodide, t-butyl chloride, t-butyl bromide, t-butyl iodide, chloromethyl alcohol, bromomethyl alcohol, iodomethyl alcohol, 1-chloroethanol, 1-bromoethanol, 1-iodoethanol, 2-chloroethanol, 2-bromoethanol, 2-iodoethanol, 1-chloropropanol, 1-bromopropanol, 1-iodopropanol, 2-chloropropanol, 2-bromopropanol, 2-iodopropanol, 3-chloropropanol, 3-bromopropanol, 3-iodopropanol, 1-chlorobutanol, 1-bromobutanol, 1-iodobutanol, 2-chlorobutanol, 2-bromobutanol, 2-iodobutanol, 3-chlorobutanol, 3-bromobutanol, 3-iodobutanol, 4-chlorobutanol, 4-bromobutanol and 4-iodobutanol.

The reaction of the polymer comprising structural units of formula (4) with the alkyl halide of formula (6) can be carried out by the conventional procedure wherein, for example, the alkyl halide is added to a solution or suspension having the polymer dissolved or suspended therein. As specific examples of the solvent, there can be mentioned ketones such as acetone, methyl ethyl ketone and methyl amyl ketone; ethers such as diethyl ether and tetrahydrofuran (THF); water; alcohols such as methanol, ethanol and propanol; aliphatic hydrocarbons such as hexane, heptane and octane; aromatic hydrocarbons such as benzene, toluene and xylene; esters such as ethyl acetate, butyl acetate, ethyl lactate, propylene glycol monomethyl ether, propylene glycol monomethyl ether acetate and cellosolve; and non-protonic polar solvents such as dimethylformamide, dimethylsulfoxide and hexamethylphosphoramide. These solvents may be used either alone or as a mixture of at least two thereof.

The reaction temperature varies depending upon the particular alkyl halide used, and is usually in the range of 20° C. to the reflux temperature of the solvent.

The amount of alkyl halide is usually in the range of 1 to 10 mols per mol of the amino group in the polymer. When the amount of alkyl halide is smaller than 1 mol, the rate of quaternization reaction is undesirably low. In contrast, the use of alkyl halide in an amount exceeding 10 mols is not advantageous from an economical viewpoint.

The polymer comprising structural units of formula (5) according to the present invention can be used as an anion exchanger. The anion exchanger is used in various fields, for example, in the form of anion exchange membrane, anion exchange resin and anion exchange fiber. The anion exchanger is especially useful in a field in which a high heat stability is required.

As will be seen from the above-mentioned explanation, the novel aminoalkoxystyrene according to the present invention can be prepared with an enhanced efficiency. From the aminoalkoxystyrene, a polymer thereof and a polymer having a quaternary ammonium group can be produced with an enhanced efficiency. The polymer having a quaternary ammonium group is suitable for an anion exchanger having a high heat stability.

The invention will now be specifically described by the following working examples, that by no means limit the scope of the invention.

Analysis and measurement of reaction products were conducted by the following methods and instruments.

(1) Elementary Analysis

Elementary analyzer: Perkin-Elmer fully automatic elementary analyzer 2400II

Oxygen flask combustion-IC measuring method using ion chromatograph IC-2001 available from Tosoh Corporation (2) Mass Spectrometry Mass spectrometer: JMS-K9

Measurement method: DI-MS (EI) analysis (3) NMR Measurement

NMR measurement instrument: VARIAN Gemini-200

(4) Ion Exchange Capacity

1) Ion Exchange Resin 5 g of resin (Cl type) was packed in a cylindrical column having an inner diameter of 2 cm and a length of 20 cm. 75 mL of 2N aqueous NaOH solution was passed through the column to thereby exchange the Cl type resin to OH type resin. Then pure water was passed through the column to remove NaOH. The washing was completed at the time when one drop of phenolphthalein indicator was added to 10 mL of the washing water and the color disappeared by adding one drop of 0.1N aqueous HCl solution. The 75 mL of 4% aqueous NaCl solution was passed through and the filtrate was collected (the amount of filtrate collected was A mL.). 25 mL of the collected filtrate was precisely measured and one drop of methyl red/methylene blue mixed liquid indicator was added to the 25 mL filtrate. Then the indicator-added liquid was titrated with 0.1N aqueous HCl solution (the titer was B mL). The ion exchange capacity was calculated according to the following equation.

$$\text{Ion exchange capacity (meq/g)} = [((B \times F)/10) \times (A/25)]/5$$

where F=factor of 0.1N—HCl

2) Ion Exchange Resin

Film (Cl type) was cut into a square specimen having a size of 10 cm×10 cm. The specimen was packed in a cylindrical column having an inner diameter of 2 cm and a length of 20 cm. 75 mL of 2N aqueous NaOH solution was passed through the column to thereby exchange the Cl type to OH type. Then pure water was passed through the column to remove NaOH. The washing was completed at the time when one drop of phenolphthalein indicator was added to 10 mL of the washing water and the color disappeared by adding one drop of 0.1N aqueous HCl solution. The 75 mL of 4% aqueous NaCl solution was passed through and the filtrate was collected (the amount of filtrate collected was A mL.). 25 mL of the collected filtrate was precisely measured and one drop of methyl red/methylene blue mixed liquid indicator was added to the 25 mL filtrate. Then the indicator-added liquid was titrated with 0.1N aqueous HCl solution (the titer was B mL). The ion exchange capacity was calculated according to the following equation.

$$\text{Ion exchange capacity (meq/m}^2) = [((B \times F)/10) \times (A/25)]/0.01$$

where F=factor of 0.1N—HCl

Example 1

Synthesis of p-(3-N,N-diethylaminopropoxy)styrene

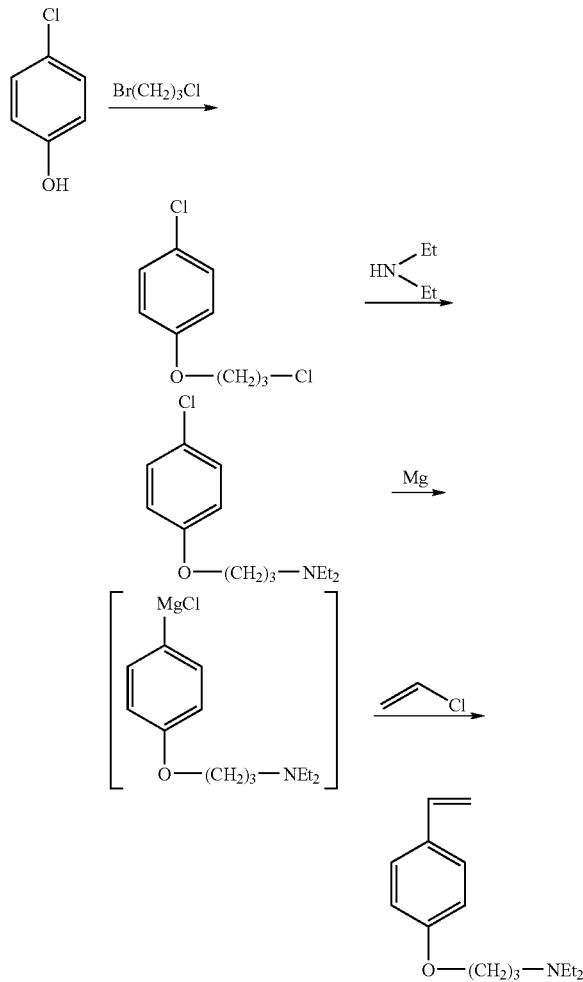

1) Synthesis of p-(3-chloropropoxy)chlorobenzene

A 1 L flask provided with a stirrer was charged with 128.6 g (1.0 mol) of p-chlorophenol (available from Tokyo Chemical Industry Co., Ltd.), 52.0 g (1.3 mols) of sodium hydroxide (available from Wako Pure Chemical Industries Ltd.), 188.9 g (1.2 mols) of 1-bromo-3-chloropropane (available from Tokyo Chemical Industry Co., Ltd.) and 300 g of water. The content was maintained at 100° C. for 6 hours. Then the reaction liquid was cooled to room temperature, and deposited NaBr, produced by side reaction, was filtered off. The organic phase was separated and subjected to distillation under reduced pressure to give 179.2 g of the target p-(3-chloropropoxy)chlorobenzene (yield: 83%, purity: 95%).

Analysis of p-(3-chloropropoxy)chlorobenzene

Mass spectroscopy (m/z): 205 ($m^+$)

Elementary analysis:

| Calculated: | C = 52.7%, H = 4.9%, Cl = 34.6%, O = 7.8% |
| Found: | C = 52.6%, H = 4.6%, Cl = 34.6%, O = 8.2% |

2) Synthesis of p-(3-N,N-diethylaminopropoxy)chlorobenzene

A 500 mL flask provided with a stirrer and a reflux condenser was charged in a nitrogen gas atmosphere with 70.2 g (0.96 mol) of diethylamine (available from Kanto Chemical Co., Inc.), 64.0 g (1.60 mols) of sodium hydroxide (available from Wako Pure Chemical Industries Ltd.), 12.8 g (0.04 mol) of n-tetrabutylammonium bromide (available from Kanto Chemical Co., Inc.) and 70.0 g of water. The content was maintained at 80° C. while being stirred. Then 164.0 g (0.80 mol) of the p-(3-chloropropoxy)chlorobenzene, synthesized at the above-mentioned step 1), was dropwise added at 80° C. over a period of 2 hours. The mixed liquid was maintained at that temperature for 20 hours while being stirred. After completion of the reaction, the phase separation was conducted and the organic phase was distilled under reduced pressure to give 135.5 g of the target p-(3-N,N-diethylaminopropoxy)chlorobenzene (yield: 60%, purity: 98%).

Analysis of p-(3-N,N-diethylaminopropoxy)chlorobenzene

Mass spectroscopy (m/z): 242 ($m^+$)

Elementary analysis:

| Calculated: | C = 64.6%, H = 8.3%, Cl = 14.7%, N = 5.8%, O = 6.6% |
| Found: | C = 64.5%, H = 8.4%, Cl = 14.7%, N = 5.9%, O = 6.5% |

$^1$H-NMR (CDCl$_3$): 1.09 (6H), 1.91-2.05 (2H), 2.53-2.70 (6H), 4.04 (2H), 6.86-6.93 (2H), 7.24-7.33 (2H)[ppm]

$^{13}$C-NMR (CDCl$_3$): 11.96, 27.16, 47.08, 49.32, 66.57, 115.68, 125.18, 129.12, 157.61 [ppm]

3) Synthesis of p-(3-N,N-diethylaminopropoxy)styrene

A 500 mL flask provided with a stirrer and a reflux condenser was charged in a nitrogen gas atmosphere with 5.6 g (0.24 mol) of metallic magnesium (cut form, 20-50 mesh size) (available from Yamaishi Metals Co., Ltd.), 20.0 g of tetrahydrofuran (available from Kanto Chemical Co., Inc.) and 1.3 g (0.012 mol) of ethyl bromide (available from Kanto Chemical Co., Inc.). The content was heated under reflux of solvent for 30 minutes. Then a solution in 30 g of tetrahydrofuran of 48.4 g (0.20 mol) of the p-(3-N,N-diethylaminopropoxy) chlorobenzene, synthesized at the above-mentioned step 2), was dropwise added at the same temperature over a period of 4 hours. The mixed liquid was maintained at that temperature for 5 hours while being stirred. Thus a solution in tetrahydrofuran of the target p-(3-N,N-diethylaminopropoxy)phenylmagnesium chloride was obtained.

Then 0.16 g (0.001 mol) of anhydrous iron chloride (FeCl$_3$) (available from Wako Pure Chemical Industries Ltd.) and 40.0 g of tetrahydrofuran were added to the solution of p-(3-N,N-diethylaminopropoxy)phenylmagnesium chloride. The reaction liquid was cooled to 10° C., and 13.8 g (0.24 mol) of vinyl chloride gas was blown into the reaction liquid at that temperature over a period of 3 hours. Then the reaction liquid was maintained at that temperature for 1 hour while being stirred. After completion of the reaction, the reaction liquid was treated with an aqueous hydrochloric acid solution and an aqueous sodium hydroxide solution, and the thus-obtained organic phase was distilled under reduced pressure to give 41.7 g of a colorless liquid compound as a fraction of 130° C./0.2 kPa. Analysis of the compound revealed that the compound was the target p-(3-N,N-diethylaminopropoxy)styrene (yield: 85% on the basis of p-(3-N,N-diethylaminopropoxy)chlorobenzene, purity: 95%).

Analysis of p-(3-N,N-diethylaminopropoxy)styrene

Mass spectroscopy (m/z): 233 (m$^+$)

Elementary analysis:

| | |
|---|---|
| Calculated: | C = 77.2%, H = 10.0%, N = 6.0%, O = 6.8% |
| Found: | C = 77.0%, H = 9.8%, N = 6.1%, O = 7.1% |

$^1$H-NMR (CDCl$_3$): 1.10 (6H), 1.99 (2H), 2.56-2.71 (6H), 4.09 (2H), 5.18 (1H), 5.66 (1H), 6.73 (1H), 6.91-7.43 (4H) [ppm]

$^{13}$C-NMR (CDCl$_3$): 12.05, 27.27, 47.12, 49.42, 66.22, 111.17, 114.42, 127.27, 130.15, 136.29, 158.88 [ppm]

Example 2

Synthesis of p-(3-N,N-dimethylaminopropoxy)styrene

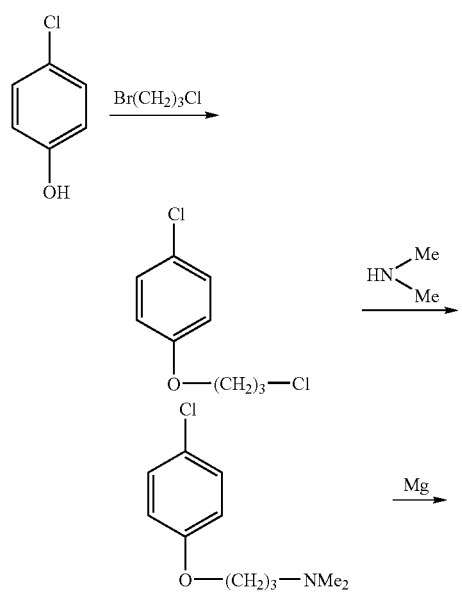

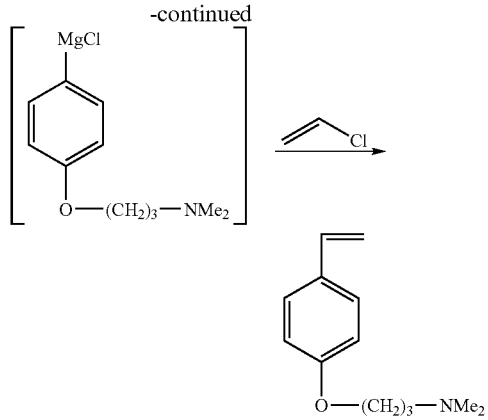

1) Synthesis of p-(3-N,N-dimethylaminopropoxy)chlorobenzene

A 500 mL flask provided with a stirrer and a reflux condenser was charged in a nitrogen gas atmosphere with 205.1 g (1.00 mol) of p-(3-chloropropoxy)chlorobenzene, synthesized by the same procedures as mentioned at the above-mentioned step 1 in Example 1), 60.0 g (1.20 mols) of sodium hydroxide (available from Wako Pure Chemical Industries Ltd.), 16.0 g (0.05 mol) of n-tetrabutylammonium bromide (available from Kanto Chemical Co., Inc.) and 100.0 g of water. The content was cooled to 10° C. while being stirred. Then 135.0 g (1.50 mol) of dimethylamine (aqueous 50% solution) (available from Wako Pure Chemical Industries Ltd.) was dropwise added to the content at the same temperature over a period of 2 hours. Thereafter the temperature of the reaction liquid was gradually elevated to room temperature, and the reaction liquid was maintained at that temperature for 20 hours while being stirred. After completion of the reaction, the phase separation was conducted and the organic phase was distilled under reduced pressure to give 184.7 g of the target p-(3-N,N-dimethylaminopropoxy)chlorobenzene (yield: 85%, purity: 98%).

Analysis of p-(3-N,N-diethylaminopropoxy)chlorobenzene

Mass spectroscopy (m/z): 213 (m$^+$)

Elementary analysis:

| | |
|---|---|
| Calculated: | C = 61.8%, H = 7.6%, Cl = 16.6%, N = 6.6%, O = 7.4% |
| Found: | C = 61.6%, H = 7.6%, Cl = 16.6%, N = 6.5%, O = 7.1% |

2) Synthesis of p-(3-N,N-dimethylaminopropoxy)styrene

A 500 mL flask provided with a stirrer and a reflux condenser was charged in a nitrogen gas atmosphere with 14.6 g (0.60 mol) of metallic magnesium (cut form, 20-50 mesh size) (available from Yamaishi Metals Co., Ltd.), 100.0 g of tetrahydrofuran (available from Kanto Chemical Co., Inc.) and 3.3 g (0.03 mol) of ethyl bromide (available from Kanto Chemical Co., Inc.). The content was heated under reflux of solvent for 30 minutes. Then 106.9 g (0.50 mol) of the p-(3-N,N-dimethylaminopropoxy)chlorobenzene, synthesized at the above-mentioned step 1), was dropwise added over a period of 4 hours. The mixed liquid was maintained at that temperature for 5 hours while being stirred. Thus a solution in tetrahydrofuran of the target p-(3-N,N-dimethylaminopropoxy)phenylmagnesium chloride was obtained.

Then 0.16 g (0.001 mol) of anhydrous iron chloride (FeCl$_3$) (available from Wako Pure Chemical Industries Ltd.) and 40.0 g of tetrahydrofuran were added to the solution of p-(3-N,N-dimethylaminopropoxy)phenylmagnesium chloride. The reaction liquid was cooled to 10° C., and 37.5 g (0.60 mol) of vinyl chloride gas was blown into the reaction liquid at that temperature over a period of 3 hours. Then the reaction liquid was maintained at that temperature for 1 hour while being stirred. After completion of the reaction, the reaction liquid was treated with an aqueous hydrochloric acid solution and an aqueous sodium hydroxide solution, and the thus-obtained organic phase was distilled under reduced pressure to give 73.8 g of a colorless liquid compound as a fraction of 115° C./0.35 kPa. Analysis of the compound revealed that the compound was the target p-(3-N,N-dimethylaminopropoxy)styrene (yield: 69% on the basis of p-(3-N,N-dimethylaminopropoxy)chlorobenzene, purity: 96%).

Analysis of p-(3-N,N-dimethylaminopropoxy)styrene

Mass spectroscopy (m/z): 205 (m$^+$)

Elementary analysis:

| Calculated: | C = 76.1%, H = 9.3%, N = 6.8%, O = 7.8% |
| --- | --- |
| Found: | C = 76.3%, H = 9.4%, N = 6.8%, O = 7.5% |

$^1$H-NMR (CDCl$_3$): 2.03 (2H), 2.33 (6H), 2.52 (2H), 4.08 (2H), 5.18 (1H), 5.66 (1H), 6.72 (1H), 6.91-7.43 (4H) [ppm]

$^{13}$C-NMR (CDCl$_3$); 27.66, 45.60, 56.46, 66.31, 111.41, 114.47, 127.29, 130.27, 136.21, 158.75 [ppm]

Example 3

Synthesis of p-(4-N,N-dimethylaminobutoxy)styrene

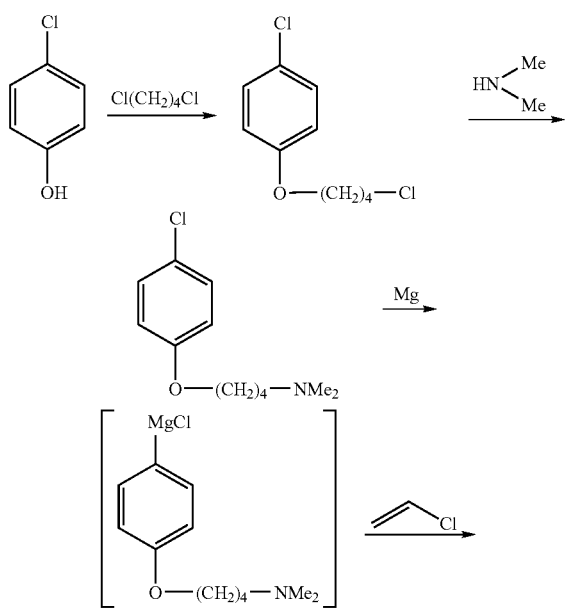

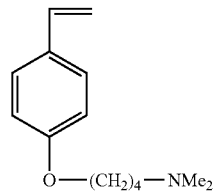

1) Synthesis of p-(4-chlorobutoxy)chlorobenzene

A 1 L flask provided with a stirrer was charged with 128.6 g (1.0 mol) of p-chlorophenol (available from Tokyo Chemical Industry Co., Ltd.), 52.0 g (1.3 mols) of sodium hydroxide (available from Wako Pure Chemical Industries Ltd.), 152.4 g (1.2 mols) of 1,4-dichlorobutane (available from Tokyo Chemical Industry Co., Ltd.) and 300 g of water. The content was maintained at 80° C. for 4 hours. Then the reaction liquid was cooled to room temperature, and deposited NaCl, produced by side reaction, was filtered off. The organic phase was separated and subjected to distillation under reduced pressure to give 177.4 g of the target p-(4-chlorobutoxy)chlorobenzene (yield: 81%, purity: 98%).

Analysis of p-(4-chlorobutoxy)chlorobenzene

Mass spectroscopy (m/z): 219 (m$^+$)

Elementary analysis:

| Calculated: | C = 54.8%, H = 5.5%, Cl = 32.4%, O = 7.3% |
| --- | --- |
| Found: | C = 54.6%, H = 5.6%, Cl = 32.2%, O = 7.6% |

2) Synthesis of p-(4-N,N-dimethylaminobutoxy)chlorobenzene

A 500 mL flask provided with a stirrer and a reflux condenser was charged in a nitrogen gas atmosphere with 109.5 g (0.50 mol) of the p-(4-chlorobutoxy)chlorobenzene, synthesized at the above-mentioned step 1), 40.0 g (1.00 mol) of sodium hydroxide (available from Wako Pure Chemical Industries Ltd.), 8.0 g (0.025 mol) of n-tetrabutylammonium bromide (available from Kanto Chemical Co., Inc.) and 50.0 g of water. The content was cooled to 10° C. while being stirred. Then 90.0 g (1.00 mol) of dimethylamine (aqueous 50% solution) (available from Wako Pure Chemical Industries Ltd.) was dropwise added at the same temperature over a period of 2 hours. Thereafter the temperature of the reaction liquid was gradually elevated to room temperature, and the reaction liquid was maintained at that temperature for 20 hours while being stirred. After completion of the reaction, the phase separation was conducted and the organic phase was distilled under reduced pressure to give 96.7 g of the target p-(4-N,N-dimethylaminobutoxy)chlorobenzene (yield: 85%, purity: 98%).

Analysis of p-(4-N,N-dimethylaminobutoxy)chlorobenzene

Mass spectroscopy (m/z): 227 (m$^+$)

Elementary analysis;

| Calculated: | C = 63.3%, H = 8.0%, Cl = 15.6%, N = 6.2%, O = 6.9% |
| --- | --- |
| Found: | C = 63.2%, H = 8.0%, Cl = 15.7%, N = 6.0%, O = 7.1% |

3) Synthesis of p-(4-N,N-dimethylaminobutoxy)styrene

A 300 mL flask provided with a stirrer and a reflux condenser was charged in a nitrogen gas atmosphere with 2.9 g (0.12 mol) of metallic magnesium (cut form, 20-50 mesh size) (available from Yamaishi Metals Co., Ltd.), 10.0 g of tetrahydrofuran (available from Kanto Chemical Co., Inc.) and 0.7 g (0.006 mol) of ethyl bromide (available from Kanto Chemical Co., Inc.). The content was heated under reflux of solvent for 30 minutes. Then a solution in 15.0 g of tetrahydrofuran of 22.7 g (0.10 mol) of the p-(4-N,N-dimethylaminobutoxy) chlorobenzene, synthesized at the above-mentioned step 2), was dropwise added at the same temperature over a period of 4 hours. The mixed liquid was maintained at that temperature for 5 hours while being stirred. Thus a solution in tetrahydrofuran of the target p-(4-N,N-dimethylaminobutoxy)phenylmagnesium chloride was obtained.

Then 0.54 g (0.001 mol) of [1,3-bis(diphenylphosphino)-propane]dichloronickel (available from Wako Pure Chemical Industries Ltd.) and 10.0 g of tetrahydrofuran were added to the solution of p-(4-N,N-dimethylaminobutoxy)phenylmagnesium chloride. The reaction liquid was cooled to 10° C., and 7.5 g (0.12 mol) of vinyl chloride gas (available from Aldrich Corporation) was blown into the reaction liquid at that temperature over a period of 2 hours. Then the reaction liquid was maintained at that temperature for 1 hour while being stirred. After completion of the reaction, the reaction liquid was treated with an aqueous hydrochloric acid solution and an aqueous sodium hydroxide solution, and the thus-obtained organic phase was subjected to silica-gel column chromatography to give 15.2 g of the target p-(4-N,N-dimethylaminobutoxy)styrene (yield: 65% on the basis of p-(4-N,N-dimethylaminobutoxy)chlorobenzene, purity: 95%).

Analysis of p-(4-N,N-dimethylaminobutoxy)styrene
Mass spectroscopy (m/z): 219 (m⁺)
Elementary analysis:

| Calculated: | C = 76.4%, H = 9.7%, N = 6.4%, O = 7.5% |
|---|---|
| Found: | C = 76.2%, H = 9.8%, N = 6.6%, O = 7.4% |

Example 4

Synthesis of m-(4-N,N-dimethylaminobutoxy)styrene

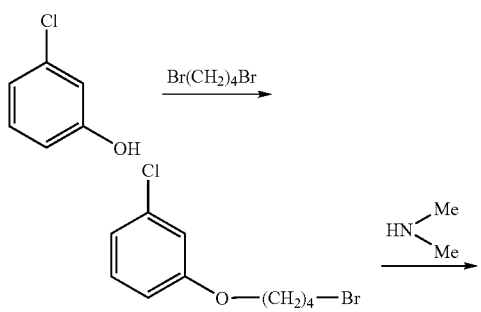

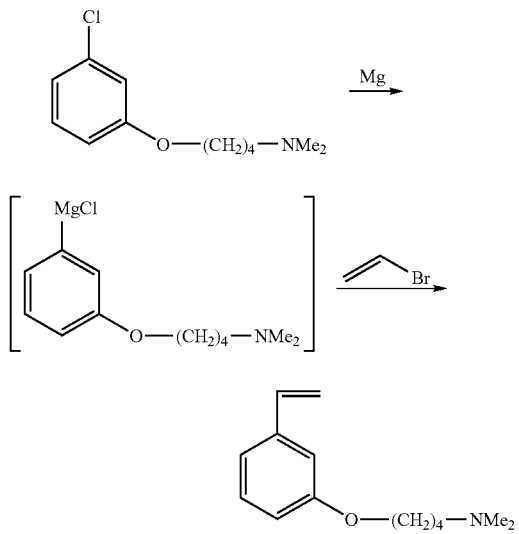

1) Synthesis of m-(4-bromobutoxy)chlorobenzene

A 1 L flask provided with a stirrer was charged with 128.6 g (1.0 mol) of m-chlorophenol (available from Tokyo Chemical Industry Co., Ltd.), 52.0 g (1.3 mols) of sodium hydroxide (available from Wako Pure Chemical Industries Ltd.), 259.1 g (1.2 mols) of 1,4-dibromobutane (available from Tokyo Chemical Industry Co., Ltd.) and 300 g of water. The content was maintained at 80° C. for 4 hours. Then the reaction liquid was cooled to room temperature, and deposited NaBr, produced by side reaction, was filtered off. The organic phase was separated and subjected to distillation under reduced pressure to give 216.9 g of the target m-(4-bromobutoxy)chlorobenzene (yield: 79%, purity: 96%).

Analysis of m-(4-bromobutoxy)chlorobenzene
Mass spectroscopy (m/z): 263 (m⁺)
Elementary analysis:

| Calculated: | C = 45.6%, H = 4.6%, Br = 30.3%, Cl = 13.5%, O = 6.0% |
|---|---|
| Found: | C = 45.8%, H = 4.6%, Br = 30.1%, Cl = 13.3%, O = 6.2% |

2) Synthesis of m-(4-N,N-dimethylaminobutoxy)chlorobenzene

A 500 mL flask provided with a stirrer and a reflux condenser was charged in a nitrogen gas atmosphere with 131.8 g (0.50 mol) of the m-(4-bromobutoxy)chlorobenzene, synthesized at the above-mentioned step 1), 40.0 g (1.00 mol) of sodium hydroxide (available from Wako Pure Chemical Industries Ltd.), 8.0 g (0.025 mol) of n-tetrabutylammonium bromide (available from Kanto Chemical Co., Inc.) and 50.0 g of water. The content was cooled to 10° C. while being stirred. Then 90.0 g (1.00 mol) of dimethylamine (aqueous 50% solution) (available from Wako Pure Chemical Industries Ltd.) was dropwise added at the same temperature over a period of 2 hours. Thereafter the temperature of the reaction liquid was gradually elevated to room temperature, and the reaction liquid was maintained at that temperature for 20 hours while being stirred. After completion of the reaction, the phase separation was conducted and the organic phase was distilled under reduced pressure to give 97.2 g of the target m-(4-N,N-dimethylaminobutoxy)chlorobenzene (yield: 83%, purity: 97%).

Analysis of m-(4-N,N-dimethylaminobutoxy)chlorobenzene

Mass spectroscopy (m/z): 227 (m$^+$)

Elementary analysis:

| Calculated: | C = 63.3%, H = 8.0%, Cl = 15.6%, N = 6.2%, O = 6.9% |
| Found: | C = 63.3%, H = 8.2%, Cl = 15.3%, N = 6.1%, O = 7.1% |

3) Synthesis of m-(4-N,N-dimethylaminobutoxy)styrene

A 300 mL flask provided with a stirrer and a reflux condenser was charged in a nitrogen gas atmosphere with 2.9 g (0.12 mol) of metallic magnesium (cut form, 20-50 mesh size) (available from Yamaishi Metals Co., Ltd.), 10.0 g of tetrahydrofuran (available from Kanto Chemical Co., Inc.) and 0.7 g (0.006 mol) of ethyl bromide (available from Kanto Chemical Co., Inc.). The content was heated under reflux of solvent for 30 minutes. Then a solution in 15.0 g of tetrahydrofuran of 22.7 g (0.10 mol) of the m-(4-N,N-dimethylaminobutoxy) chlorobenzene, synthesized at the above-mentioned step 2), was dropwise added at the same temperature over a period of 4 hours. The mixed liquid was maintained at that temperature for 5 hours while being stirred. Thus a solution in tetrahydrofuran of the target m-(4-N,N-dimethylaminobutoxy)phenylmagnesium chloride was obtained.

Then 0.54 g (0.001 mol) of [1,3-bis(diphenylphosphino)-propane]dichloronickel (available from Wako Pure Chemical Industries Ltd.) and 10.0 g of tetrahydrofuran were added to the solution of m-(4-N,N-dimethylaminobutoxy)phenylmagnesium chloride. The reaction liquid was cooled to 10° C., and 12.8 g (0.12 mol) of vinyl bromide gas (available from Aldrich Corporation) was blown into the reaction liquid at that temperature over a period of 2 hours. Then the reaction liquid was maintained at that temperature for 1 hour while being stirred. After completion of the reaction, the reaction liquid was treated with an aqueous hydrochloric acid solution and an aqueous sodium hydroxide solution, and the thus-obtained organic phase was subjected to silica-gel column chromatography to give 15.2 g of the target m-(4-N,N-dimethylaminobutoxy)styrene (yield: 66% on the basis of m-(4-N,N-dimethylaminobutoxy)chlorobenzene, purity: 95%).

Analysis of m-(4-N,N-dimethylaminobutoxy)styrene

Mass spectroscopy (m/z): 219 (m$^+$)

Elementary analysis:

| Calculated: | C = 76.4%, H = 9.7%, N = 6.4%, O = 7.5% |
| Found: | C = 76.3%, H = 9.6%, N = 6.1%, O = 8.0% |

Example 5

Synthesis of p-(6-N-methyl-N-ethylaminohexyloxy)styrene

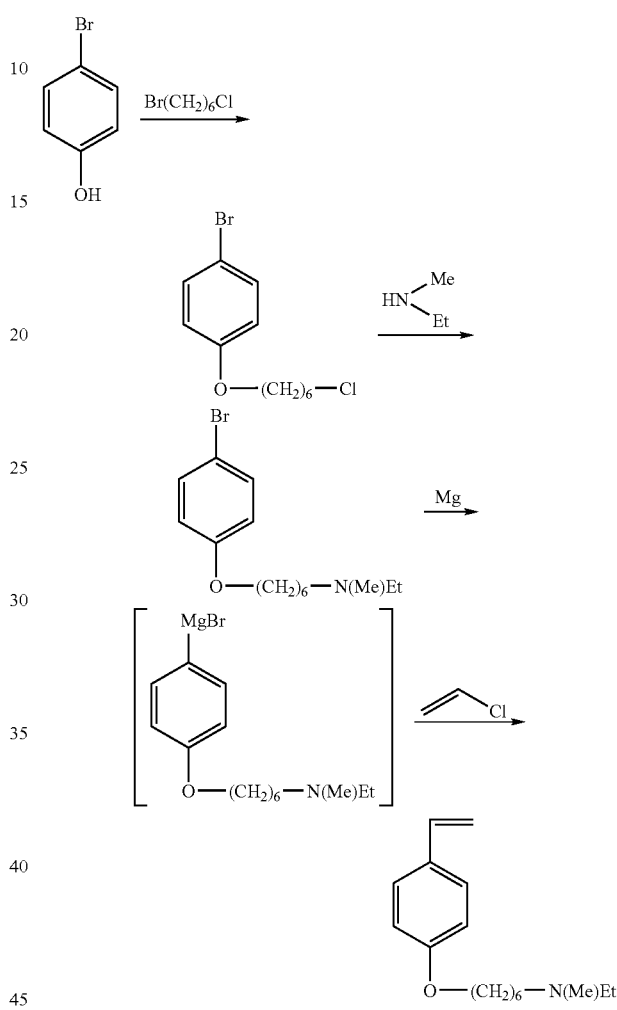

1) Synthesis of p-(6-chlorohexyloxy)bromobenzene

A 1 L flask provided with a stirrer was charged with 173.0 g (1.0 mol) of p-bromophenol (available from Tokyo Chemical Industry Co., Ltd.), 84.2 g (1.5 mols) of sodium hydroxide (available from Wako Pure Chemical Industries Ltd.), 399.0 g (2.0 mols) of 1-chloro-6-bromohexane (available from Wako Pure Chemical Industries Ltd.) and 200 g of water. The content was maintained at 100° C. for 6 hours. Then the reaction liquid was cooled to room temperature, and deposited KBr, produced by side reaction, was filtered off. The organic phase was separated and subjected to distillation under reduced pressure to give 236.9 g of the target p-(6-chlorohexyloxy) bromobenzene (yield: 78%, purity: 96%).

Analysis of p-(6-chlorohexyloxy)bromobenzene

Mass spectroscopy (m/z): 291 (m$^+$)

Elementary analysis:

| Calculated: | C = 49.4%, H = 5.5%, Br = 27.4%, Cl = 12.2%, O = 5.5% |
|---|---|
| Found: | C = 49.1%, H = 5.6%, Br = 27.7%, Cl = 12.5%, O = 5.1% |

2) Synthesis of
p-(N-methyl-N-ethylaminohexyloxy)-bromobenzene

A 100 mL flask provided with a stirrer and a reflux condenser was charged in a nitrogen gas atmosphere with 14.6 g (0.05 mol) of the p-(6-chlorohexyloxy)bromobenzene, synthesized at the above-mentioned step 1), 4.0 g (0.10 mol) of sodium hydroxide (available from Wako Pure Chemical Industries Ltd.), 0.8 g (0.012 mol) of n-tetrabutylammonium bromide (available from Kanto Chemical Co., Inc.) and 5.0 g of water. The content was maintained at 40° C. while being stirred. Then 5.9 g (0.10 mol) of methylethylamine (available from Wako Pure Chemical Industries Ltd.) was dropwise added at the same temperature over a period of 2 hours. Thereafter the reaction liquid was maintained at that temperature for 20 hours while being stirred. After completion of the reaction, the phase separation was conducted and the organic phase was subjected to silica-gel column chromatography to give 13.4 g of the target p-(N-methyl-N-ethylaminohexyloxy)bromobenzene (yield: 80%, purity: 94%).

Analysis of p-(N-methyl-N-ethylaminohexyloxy)-bromobenzene

Mass spectroscopy (m/z): 314 (m$^+$)
Elementary analysis:

| Calculated: | C = 57.3%, H = 7.7%, Br = 25.4%, N = 4.6%, O = 5.0% |
|---|---|
| Found: | C = 57.3%, H = 7.4%, Br = 25.2%, N = 4.8%, O = 5.3% |

3) Synthesis of
p-(N-methyl-N-ethylaminohexyloxy)styrene

A 200 mL flask provided with a stirrer and a reflux condenser was charged in a nitrogen gas atmosphere with 1.2 g (0.05 mol) of metallic magnesium (cut form, 20-50 mesh size) (available from Yamaishi Metals Co., Ltd.), 20.0 g of tetrahydrofuran (available from Kanto Chemical Co., Inc.) and 0.3 g (0.003 mol) of ethyl bromide (available from Kanto Chemical Co., Inc.). The content was heated under reflux of solvent for 30 minutes. Then the reaction liquid was cooled to 5° C., and a solution in 30.0 g of tetrahydrofuran of 15.7 g (0.05 mol) of the p-(N-methyl-N-ethylaminohexyloxy)bromobenzene, synthesized at the above-mentioned step 2), was dropwise added at 5° C. over a period of 1 hour. The mixed reaction liquid was maintained at that temperature for 2 hours while being stirred. Thus a solution in tetrahydrofuran of the target p-(N-methyl-N-ethylaminohexyloxy)phenylmagnesium bromide was obtained.

Then 0.16 g (0.001 mol) of anhydrous cobalt chloride (available from Wako Pure Chemical Industries Ltd.) was added to the solution of p-(N-methyl-N-ethylaminohexyloxy)phenyl-magnesium bromide. Thereafter 3.8 g (0.06 mol) of vinyl chloride gas was blown into the reaction liquid at 15° C. over a period of 1 hour. Then the reaction liquid was maintained at that temperature for 0.5 hour while being stirred. After completion of the reaction, the reaction liquid was treated with an aqueous ammonium chloride solution and an aqueous sodium hydroxide solution, and the thus-obtained organic phase was subjected to silica-gel column chromatography to give 9.8 g of the target p-(N-methyl-N-ethylaminohexyloxy)styrene (yield: 72% on the basis of p-(N-methyl-N-ethylaminohexyloxy)bromobenzene, purity: 96%).

Analysis of p-(N-methyl-N-ethylaminohexyloxy)styrene
Mass spectroscopy (m/z): 261 (m$^+$)
Elementary analysis:

| Calculated: | C = 78.1%, H = 10.4%, N = 5.4%, O = 6.1% |
|---|---|
| Found: | C = 78.0%, H = 10.2%, N = 5.5%, O = 6.3% |

Reference Example 1

Production of [p-(3-N,N-dimethylaminopropoxy)styrene]-divinylbenzene copolymer

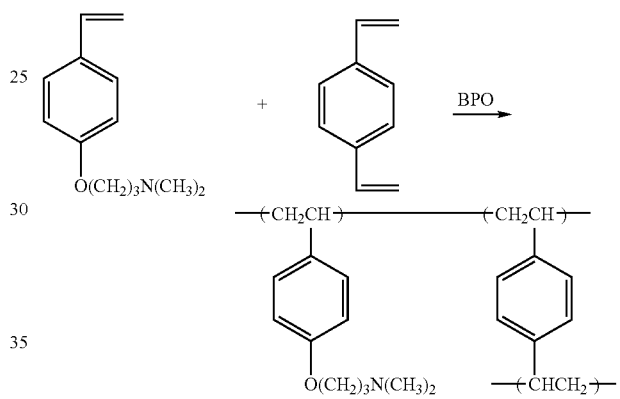

A 200 mL flask provided with a stirrer and a reflux condenser was charged in a nitrogen gas atmosphere with 100 mL of toluene, 20.5 g (0.1 mol) of p-(3-N,N-dimethylaminopropoxy) styrene, 0.95 g (0.004 mol) of industrial divinylbenzene (divinylbenzene content; 55%) and 0.2 g of benzoyl peroxide (BPO; benzoyl peroxide content: 75%). The temperature of the content was elevated to 80° C. and polymerization was carried out for 24 hours. The thus-obtained gel-like polymer solution was taken out, and washed with toluene for 10 hours using a Soxhlet extractor. Thereafter the washed polymer solution was vacuum dried at 50° C. for 24 hours to give 18.7 g of a polymer. The yield was 87%.

Example 6

Production of Quaternary Ammonium Group-Containing Polymer

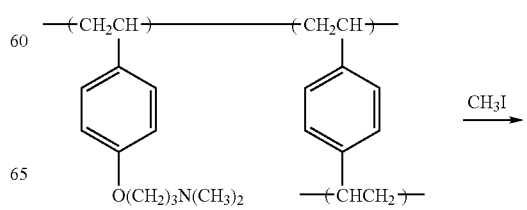

-continued

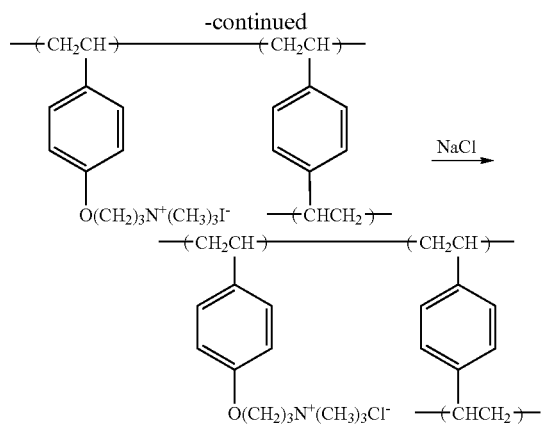

A 200 mL flask provided with a stirrer and a reflux condenser was charged in a nitrogen gas atmosphere with 100 mL of tetrahydrofuran, and 10.8 g of the polymer (amino group content: 0.05 mol; pulverized product of the polymer produced in Reference Example 1). The content was stirred at room temperature for 3 hours whereby the polymer was swollen. Then 21.3 g (0.15 mol) of iodomethane was added to the content, and the content was heated under reflux for 10 hours whereby amino groups of the polymer was quaternized. After completion of the quaternization reaction, the polymer was collected by filtration. The collected polymer washed with 100 mL of methanol three times to remove excessive iodomethane. Thereafter an aqueous 4% sodium chloride solution in an amount of 10 times the amount of the polymer was passed whereby the counter ion was changed from I type to Cl type. The polymer was vacuum dried at 50° C. for 24 hours to give 12.7 g of a quaternary ammonium group-containing polymer. The ion exchange capacity of the quaternary ammonium group-containing polymer was 4.12 meq/g.

Heat Resistance Test

A 200 mL flask provided with a reflux condenser was charged in a nitrogen gas atmosphere with 100 g of an aqueous 10% sodium hydroxide solution and 10.0 g of the quaternary ammonium group-containing polymer having a counter ion changed from I type to Cl type. The content was maintained at 100° C. for 15 days. Thereafter the polymer was collected by filtration. The ion exchange capacity was measured. The ion exchange capacity was 3.83 meq/g. Thus, the reduction percent in ion exchange capacity of the quaternary ammonium group-containing polymer caused by the heating was 7%.

Reference Example 2

Production of [p-(4-N,N-dimethylaminobutoxy)styrene]-divinylbenzene copolymer

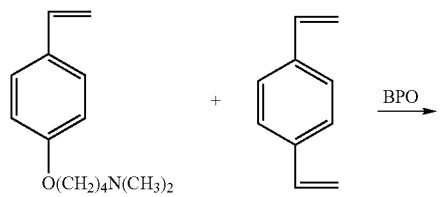

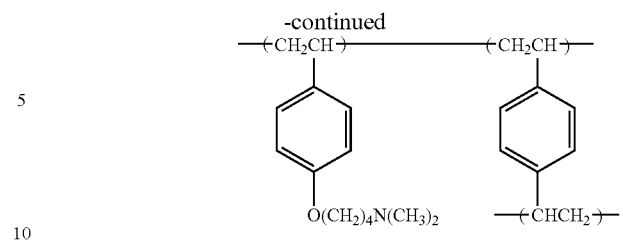

A 200 mL flask provided with a stirrer and a reflux condenser was charged in a nitrogen gas atmosphere with 100 mL of toluene, 21.9 g (0.1 mol) of p-(4-N,N-dimethylaminobutoxy)styrene, 0.95 g (0.004 mol) of industrial divinylbenzene (divinylbenzene content: 55%) and 0.2 g of benzoyl peroxide (BPO; benzoyl peroxide content: 75%). The temperature of the content was elevated to 80° C. and polymerization was carried out for 24 hours. The thus-obtained gel-like polymer solution was taken out, and washed with toluene for 10 hours using a Soxhlet extractor. Thereafter the washed polymer solution was vacuum dried at 50° C. for 24 hours to give 18.9 g of a polymer. The yield was 88%.

Example 7

Production of Quaternary Ammonium Group-Containing Polymer

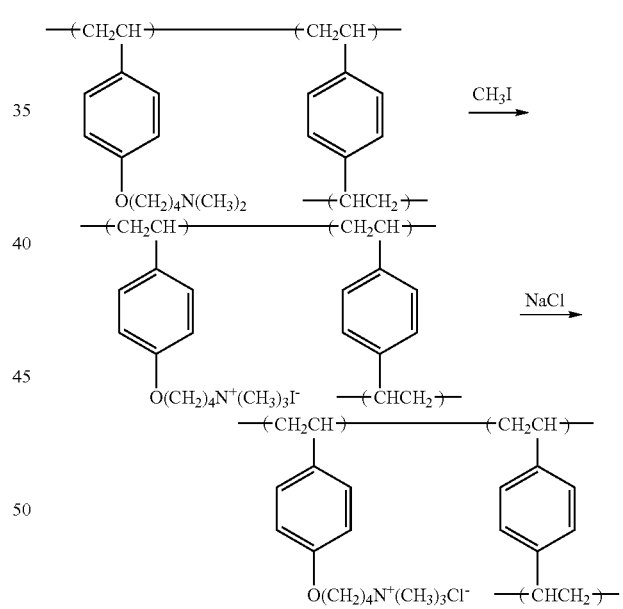

A 200 mL flask provided with a stirrer and a reflux condenser was charged in a nitrogen gas atmosphere with 100 mL of tetrahydrofuran, and 10.9 g of the polymer (amino group content: 0.05 mol; pulverized product of the polymer produced in Reference Example 2). The content was stirred at room temperature for 3 hours whereby the polymer was swollen. Then 21.3 g (0.15 mol) of iodomethane was added to the content, and the content was heated under reflux for 10 hours whereby amino groups of the polymer was quaternized. After completion of the quaternization reaction, the polymer was collected by filtration. The collected polymer washed with 100 mL of methanol three times to remove excessive iodomethane. Thereafter an aqueous 4% sodium chloride solution in an amount of 10 times the amount of the polymer was passed whereby the counter ion was changed from I type to Cl type. The polymer was vacuum dried at 50° C. for 24 hours to give 12.7 g of a quaternary ammonium group-containing polymer. The ion exchange capacity of the quaternary ammonium group-containing polymer was 4.12 meq/g.

Heat Resistance Test

An aqueous 4% sodium hydroxide solution in an amount of 10 times the amount of the above-mentioned quaternary ammonium group-containing polymer was passed through 10.0 g of the polymer whereby the counter ion was changed from Cl type to OH type.

A 200 mL flask provided with a reflux condenser was charged in a nitrogen gas atmosphere with 100 g of an aqueous 10% sodium hydroxide solution and 10.0 g of the quaternary ammonium group-containing polymer having a counter ion changed from Cl type to OH type. The content was maintained at 100° C. for 60 days. Thereafter the polymer was collected by filtration. An aqueous 4% sodium chloride solution in an amount of 10 times the amount of the polymer was passed through the polymer whereby the counter ion was changed from OH type to Cl type. The ion exchange capacity was measured. The ion exchange capacity was 3.71 meq/g. Thus, the reduction percent in ion exchange capacity of the quaternary ammonium group-containing polymer caused by the heating was 10%, Comparative Example 1

Production of (trimethylaminomethylstyrene)-divinylbenzene copolymer

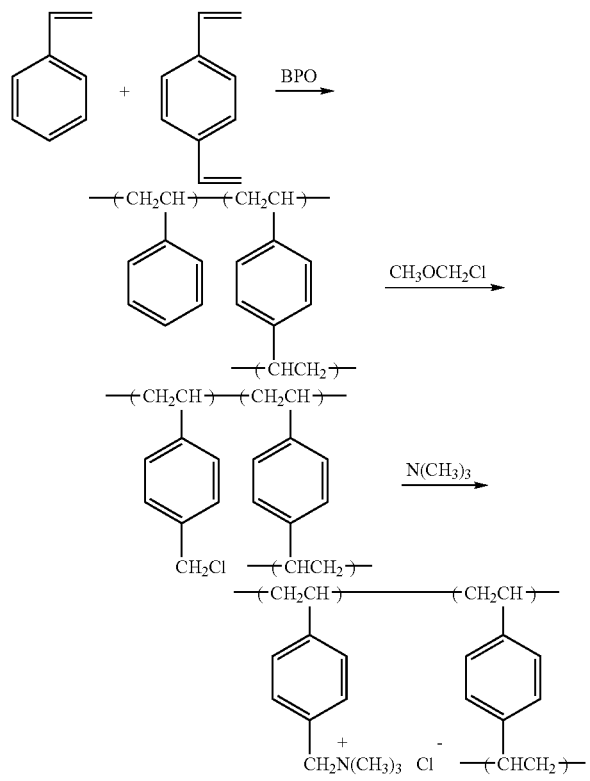

A 200 mL flask provided with a stirrer and a reflux condenser was charged in a nitrogen gas atmosphere with 100 mL of toluene, 10.4 g (0.1 mol) of styrene, 0.95 g (0.004 mol) of industrial divinylbenzene (divinylbenzene content: 55%) and 0.2 g of benzoyl peroxide (BPO; benzoyl peroxide content: 75%). The temperature of the content was elevated to 80° C. and polymerization was carried out for 24 hours. The thus-obtained gel-like polymer solution was taken out, and washed with toluene for 10 hours using a Soxhlet extractor. Thereafter the washed polymer solution was vacuum dried at 50° C. for 24 hours to give 10.0 g of a polymer.

A 300 mL flask provided with a stirrer and a reflux condenser was charged in a nitrogen gas atmosphere with 20 mL of toluene, and 10.0 g of the polymer (a pulverized product of the polymer obtained by the above-mentioned polymerization). The content was stirred at room temperature for 3 hours whereby the polymer was swollen. Then 20.0 g (0.25 mol) of chloromethyl methyl ether and 5 g (0.03 mol) of zinc chloride were added to the content, and the content was maintained at 50° C. for 5 hours to be thereby chloromethylated. After completion of the chloromethylation, 200 mL of water was added to the polymer solution to decompose excessive chloromethyl methyl ether, and the thus-chloromethylated polymer was collected by filtration.

A 200 mL flask provided with a stirrer and a reflux condenser was charged with the chloromethylated polymer and 50 mL of an aqueous 30% trimethylamine solution (trimethylamine: 0.25 mol). The content was maintained at 60° C. for 4 hours to be thereby quaternized. After completion of the quaternization, the polymer was collected by filtration, and washed with 100 mL of methanol three times. Thereafter the washed polymer was vacuum dried at 50° C. for 24 hours to give 20.15 g of a polymer. The ion exchange capacity of the polymer was 4.33 meq/g.

Heat Resistance Test 1

A 200 mL flask provided with a reflux condenser was charged in a nitrogen gas atmosphere with 10.0 g of an aqueous 10% sodium hydroxide solution and 10.0 g of the above-mentioned quaternary ammonium group-containing polymer. The content was maintained at 100° C. for 15 days. Thereafter the polymer was collected by filtration. The ion exchange capacity was measured. The ion exchange capacity was 3.12 meq/g. Thus, the reduction percent in ion exchange capacity of the quaternary ammonium group-containing polymer caused by the heating was 28%.

Heat Resistance Test 2

An aqueous 4% sodium hydroxide solution in an amount of 10 times the amount of the above-mentioned quaternary ammonium group-containing polymer was passed through 10.0 g of the polymer whereby the counter ion was changed from Cl type to OH type.

A 200 mL flask provided with a reflux condenser was charged in a nitrogen gas atmosphere with 100 g of an aqueous 10% sodium hydroxide solution and 10.0 g of the quaternary ammonium group-containing polymer having a counter ion changed from Cl type to OH type. The content was maintained at 100° C. for 60 days. Thereafter the polymer was collected by filtration. An aqueous 4% sodium chloride solution in an amount of 10 times the amount of the polymer was passed through the polymer whereby the counter ion was changed from OH type to Cl type. The ion exchange capacity was measured. The ion exchange capacity was 1.86 meq/g.

Thus, the reduction percent in ion exchange capacity of the quaternary ammonium group-containing polymer caused by the heating was 57%.

Comparative Example 2

Production of p-(N,N-dimethylaminoethoxy)styrene-divinylbenzene copolymer

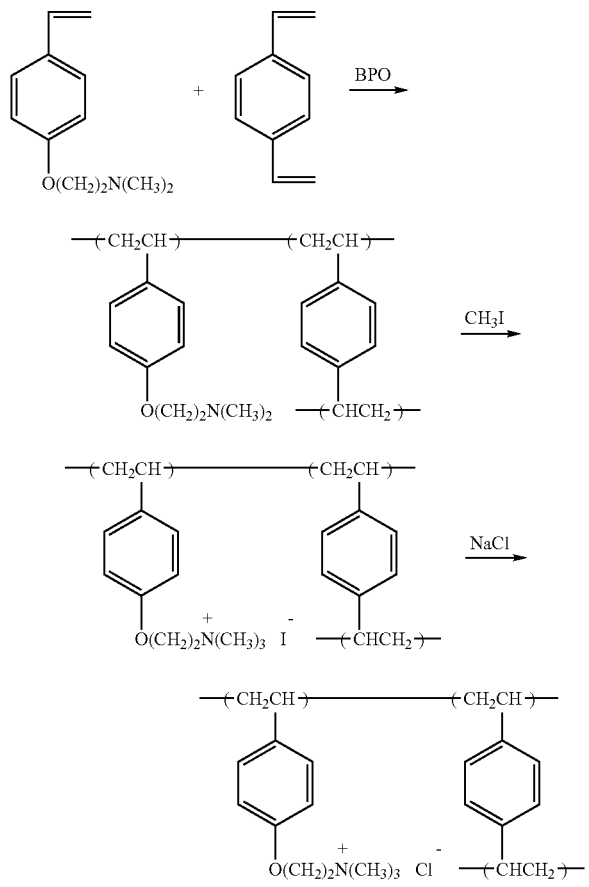

A 200 mL flask provided with a stirrer and a reflux condenser was charged in a nitrogen gas atmosphere with 100 mL of toluene, 19.1 g (0.1 mol) of p-(N,N-dimethylaminoethoxy) styrene, 0.95 g (0.004 mol) of industrial divinylbenzene (divinylbenzene content: 55%) and 0.2 g of benzoyl peroxide (BPO; benzoyl peroxide content: 75%). The temperature of the content was elevated to 80° C. and polymerization was carried out for 24 hours. The thus-obtained gel-like polymer solution was taken out, and washed with toluene for 10 hours using a Soxhlet extractor. Thereafter the washed polymer solution was vacuum dried at 50° C. for 24 hours to give 17.6 g of a polymer.

A 200 mL flask provided with a stirrer and a reflux condenser was charged in a nitrogen gas atmosphere with 100 mL of tetrahydrofuran, and 10.0 g of the polymer (amino group content: 0.05 mol; a pulverized product of the polymer obtained by the above-mentioned polymerization). The content was stirred at room temperature for 3 hours whereby the polymer was swollen. Then 21.3 g (0.15 mol) of iodomethane was added to the content, and the content was heated under reflux for 10 hours whereby amino groups of the polymer was quaternized. After completion of the quaternization reaction, the polymer was collected by filtration. The collected polymer washed with 100 mL of methanol three times to remove excessive iodomethane. Thereafter an aqueous 4% sodium chloride solution in an amount of 10 times the amount of the polymer was passed whereby the counter ion was changed from I type to Cl type. The polymer was vacuum dried at 50° C. for 24 hours to give 11.3 g of a quaternary ammonium group-containing polymer. The ion exchange capacity of the quaternary ammonium group-containing polymer was 4.01 meq/g.

Heat Resistance Test 1

A 200 mL flask provided with a reflux condenser was charged in a nitrogen gas atmosphere with 100 g of an aqueous 10% sodium hydroxide solution and 10.0 g of the above-mentioned quaternary ammonium group-containing polymer. The content was maintained at 100° C. for 15 days. Thereafter the polymer was collected by filtration. The ion exchange capacity was 2.05 meq/g. Thus, the reduction percent in ion exchange capacity of the quaternary ammonium group-containing polymer caused by the heating was 49%.

Heat Resistance Test 2

An aqueous 4% sodium hydroxide solution in an amount of 10 times the amount of the above-mentioned quaternary ammonium group-containing polymer was passed through 10.0 g of the polymer whereby the counter ion was changed from Cl type to OH type.

A 200 mL flask provided with a reflux condenser was charged in a nitrogen gas atmosphere with 100 g of an aqueous 10% sodium hydroxide solution and 10.0 g of the quaternary ammonium group-containing polymer having a counter ion changed from Cl type to OH type. The content was maintained at 100° C. for 60 days. Thereafter the polymer was collected by filtration. An aqueous 4% sodium chloride solution in an amount of 10 times the amount of the polymer was passed through the polymer whereby the counter ion was changed from OH type to Cl type. The ion exchange capacity was 1.28 meq/g. Thus, the reduction percent in ion exchange capacity of the quaternary ammonium group-containing polymer caused by the heating was 68%.

Example 8

Production of p-(3-N,N-dimethylaminopropoxy)styrene-Grafted polyethylene Film, and Quaternization Thereof A polyethylene film (12 cm×18 cm) having a thickness of 50 μm was irradiated under vacuum with electronic rays in a dose of 100 kGy. Then the film was immersed in a solution of 20.5 g of p-(3-N,N-dimethylaminopropoxy)styrene in 20.5 g of dioxane. The solution was maintained at 50° C. for 5 hours to conduct a graft polymerization reaction. After completion of the reaction, the film was taken out and washed with 100 mL of dichloromethane. The washed film was vacuum dried at 50° C. for 24 hours. The graft ratio was 6.9%. The graft ratio refers to a ratio (%) of weight increase as expressed by (B−A)/A wherein A is the weight of film as measured before the graft polymerization and B is the weight of film as measured after the graft polymerization.

A 200 mL flask provided with a reflux condenser was charged in a nitrogen gas atmosphere with 100 mL of tetrahydrofuran, the above-mentioned p-(3-N,N-dimethylaminopropoxy)styrene-grafted polyethylene film, and 2.8 g (0.02 mol) of iodomethane. The content was heated under reflux for 10 hours whereby amino groups of the polymer was quaternized. After completion of the quaternization reaction, the film was taken, and then washed with 100 mL of methanol three times to remove excessive iodomethane. Thereafter the film was washed with 100 mL of an aqueous 4% sodium chloride solution three times whereby the counter ion was changed from I type to Cl type. The film was vacuum dried at 50° C. for 24 hours. The ion exchange capacity of the quaternary ammonium group-containing polymer film was 3.08 meq/m$^2$.

Heat Resistance Test

A 200 mL flask provided with a reflux condenser was charged in a nitrogen gas atmosphere with 100 g of an aqueous 10% sodium hydroxide solution and the above-mentioned quaternary ammonium group-containing polymer film. The content was maintained at 100° C. for 15 days. Thereafter the film was collected by filtration. The ion exchange capacity was 2.93 meq/m$^2$. Thus, the reduction percent in ion exchange capacity of the quaternary ammonium group-containing polymer film caused by the heating was 5%.

Example 9

Production of
p-(4-N,N-dimethylaminobutoxy)styrene-Grafted
Polyethylene Film, and Quaternization Thereof A polyethylene film (12 cm×18 cm) having a thickness of 50 μm was irradiated under vacuum with electronic rays in a dose of 100 kGy. Then the film was immersed in a solution of 21.9 g of p-(4-N,N-dimethylaminobutoxy)styrene in 20.5 g of dioxane. The solution was maintained at 50° C. for 5 hours to conduct a graft polymerization reaction. After completion of the reaction, the film was taken out and washed with 100 mL of dichloromethane. The washed film was vacuum dried at 50° C. for 24 hours. The graft ratio was 7.5%. The graft ratio refers to a ratio (%) of weight increase as expressed by (B−A)/A wherein A is the weight of film as measured before the graft polymerization and B is the weight of film as measured after the graft polymerization.

A 200 mL flask provided with a reflux condenser was charged in a nitrogen gas atmosphere with 100 mL of tetrahydrofuran, the above-mentioned p-(4-N,N-dimethylaminobutoxy)styrene-grafted polyethylene film, and 2.8 g (0.02 mol) of iodomethane. The content was heated under reflux for 10 hours whereby amino groups of the polymer was quaternized. After completion of the quaternization reaction, the film was taken, and then washed with 100 mL of methanol three times to remove excessive iodomethane. Thereafter the film washed with 100 mL of an aqueous 4% sodium chloride solution three times whereby the counter ion was changed from I type to Cl type. The film was vacuum dried at 50° C. for 24 hours. The ion exchange capacity of the quaternary ammonium group-containing polymer film was 3.08 meq/m$^2$.

Heat Resistance Test

The quaternary ammonium group-containing polymer film having a Cl type counter anion washed with 100 mL of an aqueous 4% sodium hydroxide solution three times whereby the counter ion was changed from Cl type to OH type.

A 200 mL flask provided with a reflux condenser was charged in a nitrogen gas atmosphere with 100 g of an aqueous 10% sodium hydroxide solution and the above-mentioned quaternary ammonium group-containing polymer film having an OH type counter anion. The content was maintained at 100° C. for 15 days. Thereafter the film was collected by filtration. The ion exchange capacity was 2.86 meq/m$^2$. Thus, the reduction percent in ion exchange capacity of the quaternary ammonium group-containing polymer film caused by the heating was 7%.

Comparative Example 3

Production of
p-(dimethylaminomethyl)styrene-Grafted
Polyethylene Film, and Quaternization Thereof A polyethylene film (12 cm×18 cm) having a thickness of 50 μm was irradiated under vacuum with electronic rays in a dose of 100 kGy. Then the film was immersed in a solution of 16.1 g of p-(dimethylaminomethyl)styrene in 32.2 g of dioxane. The solution was maintained at 50° C. for 5 hours to conduct a graft polymerization reaction. After completion of the reaction, the film was taken out and washed with 100 mL of dichloromethane. The washed film was vacuum dried at 50° C. for 24 hours. The graft ratio was 5.8%. The graft ratio refers to a ratio (%) of weight increase as expressed by (B−A)/A wherein A is the weight of film as measured before the graft polymerization and B is the weight of film as measured after the graft polymerization.

A 200 mL flask provided with a reflux condenser was charged in a nitrogen gas atmosphere with 100 mL of tetrahydrofuran, the above-mentioned p-(dimethylaminomethyl)-styrene-grafted polyethylene film, and 2.8 g (0.02 mol) of iodomethane. The content was heated under reflux for 10 hours whereby amino groups of the polymer film was quaternized. After completion of the quaternization reaction, the film was taken, and then washed with 100 mL of methanol three times to remove excessive iodomethane. Thereafter the film washed with 100 mL of an aqueous 4% sodium chloride solution three times whereby the counter ion was changed from I type to Cl type. The film was vacuum dried at 50° C. for 24 hours. The ion exchange capacity of the quaternary ammonium group-containing polymer film was 2.77 meq/m$^2$.

Heat Resistance Test 1

A 200 mL flask provided with a reflux condenser was charged in a nitrogen gas atmosphere with 100 g of an aqueous 10% sodium hydroxide solution and the above-mentioned quaternary ammonium group-containing polymer film. The content was maintained at 100° C. for 15 days. Thereafter the film was collected by filtration. The ion exchange capacity was 2.02 meq/m$^2$. Thus, the reduction percent in ion exchange capacity of the quaternary ammonium group-containing polymer film caused by the heating was 27%.

Heat Resistance Test 2

The quaternary ammonium group-containing polymer film having a Cl type counter anion washed with 100 mL of an aqueous 4% sodium hydroxide solution three times whereby the counter ion was changed from Cl type to OH type.

A 200 mL flask provided with a reflux condenser was charged in a nitrogen gas atmosphere with 100 g of an aqueous 10% sodium hydroxide solution and the above-mentioned quaternary ammonium group-containing polymer film having an OH type counter anion. The content was maintained at 100° C. for 15 days. Thereafter the film was collected by filtration. The ion exchange capacity was 1.69 meq/m$^2$. Thus, the reduction percent in ion exchange capacity of the quaternary ammonium group-containing polymer film caused by the heating was 39%.

What is claimed is:

1. A polymer comprising structural units represented by the following general formula (4):

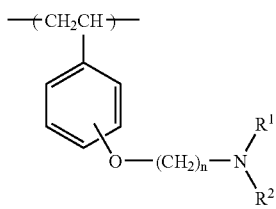

(4)

wherein $R^1$ and $R^2$ independently represent an alkyl group having 1 to 4 carbon atoms, and n is an integer of 3 to 6.

2. The polymer according to claim 1, which is a homopolymer consisting of the structural units of formula (4), or a copolymer comprising at least 1% by mol of structural units of formula (4) and not more than 99% by mol of structural units derived from at least one vinyl monomer.

3. A polymer comprising structural units represented by the following general formula (5):

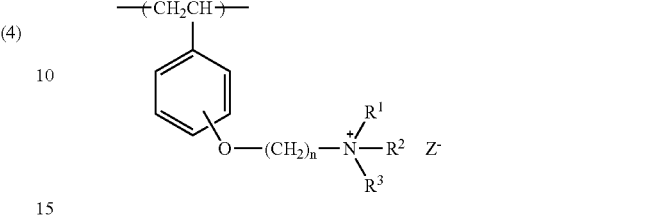

(5)

wherein $R^1$ and $R^2$ independently represent an alkyl group having 1 to 4 carbon atoms, $R^3$ represents an alkyl group having 1 to 4 carbon atoms or an alkanol group having 1 to 4 carbon atoms, Z represents an anion, and n is an integer of 3 to 6.

* * * * *